United States Patent
Kaspar

(10) Patent No.: US 10,907,130 B2
(45) Date of Patent: Feb. 2, 2021

(54) METHODS AND MATERIALS FOR PRODUCING RECOMBINANT VIRUSES IN EUKARYOTIC MICROALGAE

(71) Applicant: RESEARCH INSTITUTE AT NATIONWIDE CHILDREN'S HOSPITAL, Columbus, OH (US)

(72) Inventor: Brian K. Kaspar, Westerville, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 179 days.

(21) Appl. No.: 15/524,963

(22) PCT Filed: Nov. 5, 2015

(86) PCT No.: PCT/US2015/059272
§ 371 (c)(1),
(2) Date: May 5, 2017

(87) PCT Pub. No.: WO2016/073739
PCT Pub. Date: May 12, 2016

(65) Prior Publication Data
US 2018/0282684 A1 Oct. 4, 2018

Related U.S. Application Data

(60) Provisional application No. 62/075,408, filed on Nov. 5, 2014.

(51) Int. Cl.
*C12N 1/12* (2006.01)
*C12N 7/00* (2006.01)
*C12N 15/86* (2006.01)

(52) U.S. Cl.
CPC ............... *C12N 1/12* (2013.01); *C12N 7/00* (2013.01); *C12N 15/86* (2013.01); *C12N 2750/14122* (2013.01); *C12N 2750/14143* (2013.01); *C12N 2750/14151* (2013.01); *C12N 2800/22* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 8,211,307 B2 | 7/2012 | Chew et al. |
| 2011/0162115 A1 | 6/2011 | Guo et al. |
| 2014/0349374 A1 | 11/2014 | Galibert et al. |

FOREIGN PATENT DOCUMENTS

| | | | |
|---|---|---|---|
| WO | WO-95/13365 A1 | 5/1995 | |
| WO | WO-95/13392 A1 | 5/1995 | |
| WO | WO-96/17947 A1 | 6/1996 | |
| WO | WO-97/06243 A1 | 2/1997 | |
| WO | WO-97/08298 A1 | 3/1997 | |
| WO | WO-97/09441 A2 | 3/1997 | |
| WO | WO-97/21825 A1 | 6/1997 | |
| WO | WO-98/09657 A3 | 4/1998 | |
| WO | WO-99/11764 A3 | 6/1999 | |
| WO | WO 2005/033321 | * | 4/2005 |
| WO | WO-2013/014400 A1 | 1/2013 | |

OTHER PUBLICATIONS

Mary, Bertin, et al. "Adeno-associated Virus Vectors in Gene Therapy." Gene and Cell Therapy: Biology and Applications. Springer, Singapore, 2018. 29-56.*
Specht et al. (Frontiers in Immunology. Feb. 2014; 5 (60): 1-7).*
Anderson et al., A simple method for the rapid generation of recombinant adenovirus vectors, Gene Ther., 7(12):1034-8 (2000).
Carter, Adeno-associated virus vectors, Curr. Opin. Biotechnol., 3(5):533-9 (1992).
Clark et al., A stable cell line carrying adenovirus-inducible rep and cap genes allows for infectivity titration of adeno-associated virus vectors, Gene Therapy 3:1124-32 (1996).
Fukuda et al., Simple histone acetylation plays a complex role in the regulation of gene expression, Brief Funct. Genomic Proteomic, 5(3):190-208 (2006).
GenBank Accession No. NC_001829, Adeno-associated virus-4, complete genome, dated Jan. 28, 2010.
GenBank Accession No. AF085716, Adeno-associated virus 5 DNA binding trs helicase (Rep22) and capsid protein (VP1) genes, complete cds, dated Feb. 9, 1999.
Genbank Accession No. AX753246, Sequence 1 from Patent EP1310571, dated Jun. 23, 2003.
Genbank Accession No. AX753249, Sequence 4 from Patent EP1310571, dated Jun. 23, 2003.
GenBank Accession No. NC 001401, Adeno-associated virus-2, complete genome, Dec. 2, 2014.
GenBank Accession No. NC_00 1862, Adeno-associated virus 6, complete genome, dated Jan. 12, 2004.
GenBank Accession No. NC_002077, Adeno-associated virus-1, complete genome, dated Mar. 11, 2010.
Gillham et al., Mating type linked mutations which disrupt the uniparental transmission of chloroplast genes in chlamydomonas, Genetics, 115(4):677-84 (1987).
Gong et al., Microalgae as platforms for production of recombinant proteins and valuable compounds: progress and prospects, J. Ind. Microbiol. Biotechnol., 38(12):1879-90 (2011).

(Continued)

*Primary Examiner* — Shanon A. Foley
(74) *Attorney, Agent, or Firm* — Marshall, Gerstein & Borun LLP

(57) ABSTRACT

The present invention is directed to methods and materials for producing recombinant viruses. In particular, methods and materials are provided for producing recombinant viruses in eukaryotic microalgae such as *Chlamydomonas reinhardtii*. Recombinant adeno-associated viruses are examples of recombinant viruses produced according to the invention.

24 Claims, 9 Drawing Sheets

Specification includes a Sequence Listing.

(56) References Cited

OTHER PUBLICATIONS

Griesbeck et al., Chlamydomonas reinhardtii: a protein expression system for pharmaceutical and biotechnological proteins, Mol. Biotechnol., 34(2):213-23 (2006).
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
International Application No. PCT/US15/59272, International Preliminary Report on Patentability, dated May 9, 2017.
International Application No. PCT/US15/59272, International Search Report and Written Opinion, dated Jan. 27, 2016.
Joung et al., A bacterial two-hybrid selection system for studying protein-DNA and protein-protein interactions, Proc. Natl. Acad. Sci. USA, 97(13):7382-7 (2000).
Lebkowski et al., Adeno-associated virus: a vector system for efficient introduction and integration of DNA into a variety of mammlian cell types, Mol. Cell. Biol., 7:3988-96 (1988).
Lin et al., A comprehensive synthetic genetic interaction network governing yeast histone acetylation and deacetylation, Genes Dev., 22(15):2062-74 (2008).
Marsic et al., Vector design Tour de Force: integrating combinatorial and rational approaches to derive novel adeno-associated virus variants, Mol. Ther., 22(11):1900-9 (2014).
McLaughlin et al., Adeno-associated virus general transduction vectors: analysis of proviral structures, J. Virol., 62(6):1963-73 (1988).
Muzyczka, Use of adeno-associated virus as a general transduction vector for mammalian cells, Curr. Top Microbiol. Immunol., 158:97-129 (1992).
Paul et al., Increased viral titer through concentration of viral harvests from retroviral packaging lines, Human Gene Therapy, 4:609-15 (1993).
Perrin et al., An experimental rabies vaccine produced with a new BHK-21 suspension cell culture process: use of serum-free medium and perfusion-reactor system, Vaccine, 13:1244-50 (1995).
Rasala et al., Enhanced genetic tools for engineering multigene traits into green algae, PLoS One, 9(4):e94028 (2014).
Renthal et al., Histone acetylation in drug addiction, Semin. Cell Dev. Biol., 20(4):387-94 (2009).
Ruffing et al., Mutations in the carboxy terminus of adeno-associated virus 2 capsid proteins affect viral infectivity: lack of an RGD integrin-binding motif, J. Gen. Virol., 75 (Pt. 12):3385-92 (1994).
Samulski et al., Mutations in the carboxy terminus of adeno-associated virus 2 capsid proteins affect viral infectivity: lack of an RGD integrin-binding motif, *J. Virol.*, 63:3822-8 (1989).
Srivastava et al., Nucleotide sequence and organization of the adeno-associated virus 2 genome, J. Virol., 45(2):555-64 (1983).
Tratschin et al., A human parvovirus, adeno-associated virus, as a eucaryotic vector: transient expression and encapsidation of the procaryotic gene for chloramphenicol acetyltransferase, Mol. Cell Biol., 4(10):2072-81 (1984).
Tratschin et al., Adeno-associated virus vector for high-frequency integration, expression, and rescue of genes in mammalian cells, Mol. Cell Biol., 5(11):3251-60 (1985).
Young, Yeast two-hybrid: so many interactions, (in) so little time . . . , Biol. Reprod., 58(2):302-11 (1998).

* cited by examiner gDNA PCR with Rep78 primers

M: 1kb plus marker
Positive Clones: 1,3,7,8 gDNA PCR with VP1 primers

M: 1kb plus marker
Positive Clones: 3,7

SEQUENCE LISTING

```
<160> NUMBER OF SEQ ID NOS: 4

<210> SEQ ID NO 1
<211> LENGTH: 1866
<212> TYPE: DNA
<213> ORGANISM: Adeno-Associated Virus 9

<400> SEQUENCE: 1
atgccaggct tctacgagat cgtgatcaag gtgcccagcg acctggacga gcacctgccc      60
ggcatcagcg acagcttcgt gaactgggtg gccgagaagg agtgggagct gccccccgac     120
agcgacatgg acctgaacct gatcgagcag gccccctga ccgtggccga gaagctgcag     180
cgcgacttcc tgaccgagtg gcgccgcgtg agcaaggccc ccgaggccct gttcttcgtg     240
cagttcgaga agggcgagag ctacttccac atgcacgtgc tggtggagac caccggcgtg     300
aagagcatgg tgctgggccg cttcctgagc cagatccgcg agaagctgat ccagcgcatc     360
taccgcggca tcgagcccac cctgcccaac tggttcgccg tgaccaagac ccgcaacggc     420
gccggcggcg gcaacaaggt ggtggacgag tgctacatcc ccaactacct gctgcccaag     480
acccagcccg agctgcagtg ggcctggacc aacatggagc agtacctgag cgcctgcctg     540
aacctgaccg agcgcaagcg cctggtggcc cagcacctga cccacgtgag ccagacccag     600
gagcagaaca aggagaacca gaaccccaac agcgacgccc ccgtgatccg cagcaagacc     660
agcgcccgct acatggagct ggtgggctgg ctggtggaca agggcatcac cagcgagaag     720
cagtggatcc aggaggacca ggccagctac atcagcttca acgccgccag caacagccgc     780
agccagatca aggccgccct ggacaacgcc ggcaagatcg tgagcctgac caagaccgcc     840
cccgactacc tggtgggcca gcagcccgtg gaggacatca gcagcaaccg catctacaag     900
```

```
atcctggagc tgaacggcta cgacccccag tacgccgcca gcgtgttcct gggctgggcc      960
accaagaagt tcggcaagcg caacaccatc tggctgttcg ccccgccac caccggcaag     1020
accaacatcg ccgaggccat cgcccacacc gtgcccttct acggctgcgt gaactggacc    1080
aacgagaact tccccttcaa cgactgcgtg acaagatgg tgatctggtg ggaggagggc     1140
aagatgaccg ccaaggtggt ggagagcgcc aaggccatcc tgggcggcag caaggtgcgc   1200
gtggaccaga agtgcaagag cagcgcccag atcgacccca ccccgtgat cgtgaccagc    1260
aacaccaaca tgtgcgccgt gatcgacggc aacagcacca ccttcgagca ccagcagccc   1320
ctgcaggacc gcatgttcaa gttcgagctg acccgccgcc tggaccacga cttcggcaag   1380
gtgaccaagc aggaggtgaa ggacttcttc cgctgggcca aggaccacgt ggtggaggtg   1440
gagcacgagt tctacgtgaa gaagggcggc gccaagaagc gccccgcccc cagcgacgcc   1500
gacatcagcg agcccaagcg cgtgcgcgag agcgtggccc agcccagcac cagcgacgcc   1560
gaggccagca tcaactacgc cgaccgctac cagaacaagt gcagccgcca cgtgggcatg   1620
aacctgatgc tgttcccctg ccgccagtgc gagcgcatga ccagaacag caacatctgc    1680
ttcacccacg gccagaagga ctgcctggag tgcttccccg tgagcgagag ccagcccgtg   1740
agcgtggtga gaaggcccta ccagaagctg tgctacatcc accacatcat gggcaaggtg    1800
cccgacgcct gcaccgcctg cgacctggtg aacgtggacc tggacgactg catcttcgag   1860
cagtaa                                                                1866

<210> SEQ ID NO 2
<211> LENGTH: 1194
<212> TYPE: DNA
<213> ORGANISM: Adeno-Associated Virus 9

<400> SEQUENCE: 2
atggagctgg tgggctggct ggtggacaag ggcatcacca gcgagaagca gtggatccag     60
gaggaccagg ccagctacat cagcttcaac gccgccagca cagccgcag ccagatcaag     120
gccgccctgg acaacgccgg caagatcatg agcctgacca agaccgcccc cgactacctg    180
gtgggccagc agcccgtgga ggacatcagc agcaaccgca tctacaagat cctggagctg    240
aacggctacg accccccagta cgccgccagc gtgttcctgg gctgggccac caagaagttc    300
ggcaagcgca acaccatctg gctgttcggc cccgccacca ccggcaagac caacatcgcc    360
gaggccatcg cccacaccgt gcccttctac ggctgcgtga actggaccaa cgagaacttc    420
cccttcaacg actgcgtgga caagatggtg atctggtggg aggagggcaa gatgaccgcc    480
aaggtggtgg agagcgccaa ggccatcctg ggcggcagca aggtgcgcgt ggaccagaag    540
tgcaagagca gcgcccagat cgaccccacc ccgtgatcg tgaccagcaa caccaacatg     600
tgcgccgtga tcgacggcaa cagcaccacc ttcgagcacc agcagcccct gcaggaccgc    660
atgttcaagt tcgagctgac ccgccgcctg gaccacgact tcggcaaggt gaccaagcag    720
gaggtgaagg acttcttccg ctgggccaag gaccacgtgg tggaggtgga gcacgagttc    780
tacgtgaaga agggcggcgc caagaagcgc ccgcccca gcgacgccga catcagcgag       840
cccaagcgcg tgcgcgagag cgtggcccag cccagcacca gcgacgccga ggccagcatc    900
aactacgccg accgctacca gaacaagtgc agccgccacg tgggcatgaa cctgatgctg    960
ttcccctgcc gccagtgcga gcgcatgaac cagaacagca acatctgctt cacccacggc   1020
cagaaggact gcctggagtg cttccccgtg agcgagagcc agcccgtgag cgtggtgaag   1080
```

| | |
|---|---|
| aaggcctacc agaagctgtg ctacatccac cacatcatgg gcaaggtgcc cgacgcctgc | 1140 |
| accgcctgcg acctggtgaa cgtggacctg gacgactgca tcttcgagca gtaa | 1194 |

<210> SEQ ID NO 3
<211> LENGTH: 2211
<212> TYPE: DNA
<213> ORGANISM: Adeno-Associated Virus 9

<400> SEQUENCE: 3

| | |
|---|---|
| atggccgccg acggctacct gcccgactgg ctggaggaca acctgagcga gggcatccgc | 60 |
| gagtggtggg ccctgaagcc cggcgccccc cagcccaagg ccaaccagca gcaccaggac | 120 |
| aacgcccgcg gcctggtgct gcccggctac aagtacctgg cccccggcaa cggcctggac | 180 |
| aagggcgagc ccgtgaacgc cgccgacgcc gccgccctgg agcacgacaa ggcctacgac | 240 |
| cagcagctga aggccggcga caaccccta c ctgaagtaca accacgccga cgccgagttc | 300 |
| caggagcgcc tgaaggagga caccagcttc ggcggcaacc tgggccgcgc cgtgttccag | 360 |
| gccaagaagc gcctgctgga gccctgggc ctggtggagg aggccgccaa gaccgccccc | 420 |
| ggcaagaagc gccccgtgga gcagagcccc caggagcccg acagcagcgc cggcatcggc | 480 |
| aagagcggcg cccagcccgc caagaagcgc ctgaacttcg gccagaccgg cgacaccgag | 540 |
| agcgtgcccg accccagcc catcggcgag cccccgccg ccccagcgg cgtgggcagc | 600 |
| ctgaccatgg ccagcggcgg cggcgccccc gtggccgaca caacgagggg cgccgacggc | 660 |
| gtgggcagca gcagcggcaa ctggcactgc gacagccagt ggctgggcga ccgcgtgatc | 720 |
| accaccagca cccgcacctg ggccctgccc acctacaaca accacctgta caagcagatc | 780 |
| agcaacagca ccagcggcgg cagcagcaac gacaacgcct acttcggcta cagcaccccc | 840 |
| tggggctact cgacttcaa ccgcttccac tgccacttca gccccgcga ctggcagcgc | 900 |
| ctgatcaaca caactgggg cttccgcccc aagcgcctga acttcaagct gttcaacatc | 960 |
| caggtgaagg aggtgaccga caacaacggc gtgaagacca tcgccaacaa cctgaccagc | 1020 |
| accgtgcagg tgttcaccga cagcgactac cagctgccct acgtgctggg cagcgcccac | 1080 |
| gagggctgcc tgcccccctt ccccgccgac gtgttcatga tccccagta cggctacctg | 1140 |
| accctgaacg acggcagcca ggccgtgggc cgcagcagct ctactgcct ggagtacttc | 1200 |
| cccagccaga tgctgcgcac cggcaacaac ttccagttca gctacgagtt cgagaacgtg | 1260 |
| cccttccaca gcagctacgc ccacagccag agcctggacc gcctgatgaa ccccctgatc | 1320 |
| gaccagtacc tgtactacct gagcaagacc atcaacggca gcggccagaa ccagcagacc | 1380 |
| ctgaagttca gcgtggccgg ccccagcaac atggccgtgc agggccgcaa ctacatcccc | 1440 |
| ggccccagct accgccagca gcgcgtgagc accaccgtga cccagaacaa caacagcgag | 1500 |
| ttcgcctggc ccggcgccag cagctgggcc ctgaacggcc gcaacagcct gatgaacccc | 1560 |
| ggccccgcca tggccagcca caaggagggc gaggaccgct tcttccccct gagcggcagc | 1620 |
| ctgatcttcg gcaagcaggg caccggccgc gacaacgtgg acgccgacaa ggtgatgatc | 1680 |
| accaacgagg aggagatcaa gaccaccaac cccgtggcca ccgagagcta cggccaggtg | 1740 |
| gccaccaacc accagagcgc ccaggcccag gcccagaccg gctgggtgca gaaccagggc | 1800 |
| atcctgcccg gcatggtgtg gcaggaccgc gacgtgtacc tgcagggccc catctgggcc | 1860 |
| aagatccccc acaccgacgg caacttccac cccagccccc tgatgggcgg cttcggcatg | 1920 |
| aagcaccccc cccccagat cctgatcaag aacaccccg tgcccgccga ccccccacc | 1980 |
| gccttcaaca aggacaagct gaacagcttc atcacccagt acagcaccgg ccaggtgagc | 2040 |

| | |
|---|---|
| gtggagatcg agtgggagct gcagaaggag aacagcaagc gctggaaccc cgagatccag | 2100 |
| tacaccagca actactacaa gagcaacaac gtggagttcg ccgtgaacac cgagggcgtg | 2160 |
| tacagcgagc cccgccccat cggcacccgc tacctgaccc gcaacctgta a | 2211 |

<210> SEQ ID NO 4
<211> LENGTH: 1800
<212> TYPE: DNA
<213> ORGANISM: Adeno-Associated Virus 9

<400> SEQUENCE: 4

| | |
|---|---|
| acggccccg gcaagaagcg ccccgtggag cagagccccc aggagcccga cagcagcgcc | 60 |
| ggcatcggca gagcggcgc ccagcccgcc aagaagcgcc tgaacttcgg ccagaccggc | 120 |
| gacaccgaga gcgtgcccga ccccagccc atcggcgagc ccccgccgc cccagcggc | 180 |
| gtgggcagcc tgaccatggc cagcggcggc ggcgcccccg tggccgacaa caacgagggc | 240 |
| gccgacggcg tgggcagcag cagcggcaac tggcactgcg acagccagtg gctgggcgac | 300 |
| cgcgtgatca ccaccagcac ccgcacctgg gccctgccca cctacaacaa ccacctgtac | 360 |
| aagcagatca gcaacagcac cagcggcggc agcagcaacg acaacgccta cttcggctac | 420 |
| agcacccccct ggggctactt cgacttcaac cgcttccact gccacttcag ccccgcgac | 480 |
| tggcagcgcc tgatcaacaa caactggggc ttccgcccca gcgcctgaa cttcaagctg | 540 |
| ttcaacatcc aggtgaagga ggtgaccgac aacaacggcg tgaagaccat cgccaacaac | 600 |
| ctgaccagca ccgtgcaggt gttcaccgac agcgactacc agctgcccta cgtgctgggc | 660 |
| agcgcccacg agggctgcct gccccccttc cccgccgacg tgttcatgat ccccagtac | 720 |
| ggctacctga ccctgaacga cggcagccag gccgtgggcc gcagcagctt ctactgcctg | 780 |
| gagtacttcc ccagccagat gctgcgcacc ggcaacaact ccagttcag ctacgagttc | 840 |
| gagaacgtgc ccttccacag cagctacgcc cacagccaga gcctggaccg cctgatgaac | 900 |
| cccctgatcg accagtacct gtactacctg agcaagacca tcaacggcag cggccagaac | 960 |
| cagcagaccc tgaagttcag cgtggccggc cccagcaaca tggccgtgca gggccgcaac | 1020 |
| tacatccccg gccccagcta ccgccagcag cgcgtgagca ccaccgtgac ccagaacaac | 1080 |
| aacagcgagt tcgcctggcc cggcgccagc agctgggccc tgaacggccg caacagcctg | 1140 |
| atgaacccg ccccgccat ggccagccac aaggagggcg aggaccgctt cttccccctg | 1200 |
| agcggcagcc tgatcttcgg caagcagggc accggccgcg acaacgtgga cgccgacaag | 1260 |
| gtgatgatca ccaacgagga ggagatcaag accaccaacc ccgtggccac cgagagctac | 1320 |
| ggccaggtgg ccaccaacca ccagagcgcc caggcccagg cccagaccgg ctgggtgcag | 1380 |
| aaccagggca tcctgcccgg catggtgtgg caggaccgcg acgtgtacct gcagggcccc | 1440 |
| atctgggcca agatccccca caccgacggc aacttccacc ccagccccct gatgggcggc | 1500 |
| ttcggcatga agcaccccc ccccagatc ctgatcaaga acacccccgt gcccgccgac | 1560 |
| ccccccaccg ccttcaacaa ggacaagctg aacagcttca tcacccagta cagcaccggc | 1620 |
| caggtgagcg tggagatcga gtgggagctg cagaaggaga acagcaagcg ctggaacccc | 1680 |
| gagatccagt acaccagcaa ctactacaag agcaacaacg tggagttcgc cgtgaacacc | 1740 |
| gagggcgtgt acagcgagcc ccgccccatc ggcacccgct acctgacccg caacctgtaa | 1800 |

METHODS AND MATERIALS FOR PRODUCING RECOMBINANT VIRUSES IN EUKARYOTIC MICROALGAE

This application claims priority benefit of U.S. Provisional Patent Application No. 62/075,408 filed Nov. 5, 2014, which is incorporated by reference herein in its entirety.

FIELD OF THE INVENTION

The present invention is directed to methods and materials for producing recombinant viruses. In particular, methods and materials are provided for producing recombinant viruses in eukaryotic microalgae such as *Chlamydomonas reinhardtii*. Recombinant adeno-associated viruses are examples of recombinant viruses produced according to the invention.

BACKGROUND

Microalgae are unicellular, eukaryotic, photosynthetic microorganisms which have been successfully utilized to produce a variety of human recombinant proteins. The excellence of algal systems, for the mass production of human therapeutics, lies in their inherent low cost of goods and capitalization costs. With their simple production process and faster growth rate, microalgae like *Chlamydomonas reinhardtii* can be grown in as little as four weeks at the flask scale, with the potential to scale up to 64,000 liters in another four to six weeks. Being phototrophic organisms, transgenic microalgae are suitable for growth in indoor photobioreactors as well as outdoor raceway ponds. With the help of various tools of genetic manipulation, stable transgenic lines of microalgae can be generated in as little as ten days and further scaled up to large production volumes within few weeks. Microalgae also possess complex post-transcriptional modification pathways and thus can produce properly glycosylated proteins. Due to the uniform size and type, the purification of the recombinant proteins from algal systems is relatively simple compared to other systems.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., J Virol, 45: 555-564 (1983) as corrected by Ruffing et al., J Gen Virol, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

In recent years, the use of AAV as a gene therapy vector has been the subject of increasing interest. This is because of the ability of AAV to infect both dividing as well as non-dividing cells and to target multiple cell types within peripheral tissues and central nervous system, and its relatively low risk of pathogenicity to humans. Despite these advantages AAV-based gene therapy, like other virus-based approaches, faces the need for large scale vector production to enable human administration at an affordable price.

Mammalian expression systems, for example systems in HEK293 cells, are the current gold standard for gene therapy and vaccine vector production. HEK293 cells are grown either in adherent or suspension manner. Adherent culture systems suffer from the inability to be readily scaled up. This restriction can be overcome to a limited extent by utilizing suspension culture systems. Recently, baculoviral expression systems in insect cells are also being investigated for obtaining higher yields of viral vector production, although this system is also restricted due to its genetic and physical instability. Thus, all of these systems suffer from high production costs which are directly proportional to the scale of production.

To address the issues of scalability and cost-effectiveness, alternative methods for gene therapy vector and vaccine vector production are needed in the art.

SUMMARY OF INVENTION

The present invention contemplates an eukaryotic microalgal system for producing recombinant viruses for use as gene therapy vectors or vaccine vectors. The recombinant viruses contemplated are not identical to any naturally-occurring virus. The advantages of the microalgal system include ease of culturing and maintenance, low production cost and simple purification process, rapid scalability to larger volumes and ability to support large scale viral replication and packaging.

The invention provides for an eukaryotic microalgae that produces a recombinant virus, wherein the recombinant virus is a viral vaccine vector or a viral gene therapy vector. The eukaryotic microalgae of the invention include green algae, diatoms, dinoflagellates and red algae. For example the microalgae of the invention are *Chlamydomonas* sp such as are *Chlamydomonas reinhardtii*, *Chlorella* sp such as *Chlorella vulgaris*, *Chlorella ellipsoidea*, *Chlorella sorokiniana* and *Chlorella kessleri*, *Volvox* sp. such as *Volvox carteri*, *Dunaliella* sp. such as *Dunaliella salina*, *Ostreococcus* sp. such as *Ostreococcus tauri*, *Phaeodactylum* sp. such as *Phaeodactylum tico* and *Phaeodactylum tricornutum*, *Gonium* sp. such as *Gonium pectoral*, and *Cyanidiosschyzon* sp. such as *Cyanidiosschyzon merolae*, *Haematococcus* sp. such as *Haematococcus pluvialis*, *Porphyridium* spp., *Chlorarachniophytes* and *Lotharella* sp. such as *Lotharella amoebiformis* The eukaryotic microalgae of the invention are diatoms such as *Cyclotella cryptica*, *Navicula saprophila*, *Phaeodactylum tricornutum*, *Thalassiosira weissflogii*, *Cylindrotheca fusiformis* and *Chaetoceros* sp. The microalgae of the invention are dinoflagellates such as *Amphidinium* or *Symbiodinium microadriaticum*. The microalgae of the invention are euglenoids such as *Euglena gracilis*. In a particular embodiment, the eukaryotic microalgae of the invention is *Chlamydomonas reinhardtii*.

In any of the eukaryotic microalgae of the invention, the eukaryotic microalgae produces a recombinant virus that is a replication-restricted poxvirus, replication-restricted adenovirus, influenza virus, replication-incompetent alphavirus, parvovirus (e.g., AAV), adenovirus, retrovirus, lentivirus, attenuated flavivirus, or herpesvirus.

In a particular embodiment, the eukaryotic microalgae produces recombinant adeno associated virus (rAAV). For example, the eukaryotic microalgae is transformed with a polynucleotide construct comprising a polynucleotide sequence encoding Rep 78 protein, Rep 52 protein, VP1 protein or VP2/3 protein, and the construct optionally further comprises an AAV inverted terminal repeat (ITR) and 3' AAV ITR flanking the desired product sequence, and optionally helper functions for generating a productive AAV infection. The eukaryotic microalgae is transformed with a polynucleotide construct comprising one or more polynucleotide sequences encoding Rep 78 protein, Rep 52 protein, VP1 protein and VP2/VP3 protein, and the construct optionally further comprises an AAV inverted terminal repeat (ITR) and 3' AAV ITR flanking the desired product sequence, and helper functions for generating a productive AAV infection, and optionally helper functions for generating a productive AAV infection. In addition, the eukaryotic microalgae is transformed with a polynucleotide construct comprising one or more polynucleotide sequences encoding Rep 78 protein, Rep 52 protein, VP1 protein, VP2 protein and VP3 protein, and the construct optionally further comprises an AAV inverted terminal repeat (ITR) and 3' AAV ITR flanking the desired product sequence, and optionally helper functions for generating a productive AAV infection. The polynucleotide constructs that transform the eukaryotic microalgae of the invention may express VP2/VP3 protein under a single promoter or may express VP2 protein and VP3 protein under separate promoters. Alternatively, the eukaryotic microalgae is transformed with multiple polynucleotide constructs (one or more polynucleotide constructs), each comprising at least one polynucleotide sequence encoding Rep 78 protein, Rep 52 protein, VP1 protein, VP2/3 protein, VP2 protein or VP3 protein, and one or more of the polynucleotide constructs may optionally further comprise an AAV inverted terminal repeat (ITR) and 3' AAV ITR flanking the desired product sequence, and helper functions for generating a productive AAV infection. Any of the eukaryotic microalgae of the invention produce a recombinant virus that is AAV1, AAV2, AAV3, AAV4, AAV5, AAV6, AAV7, AAV8, AAV9, AAV10, AAV11, AAV12 or AAV13. In a particular embodiment, the eukaryotic microalgae produces a recombinant virus that is AAV9.

In any of the eukaryotic microalgae of the invention, the microalgae is transformed with a polynucleotide construct comprising a nucleotide sequence encoding a heterologous protein such as a marker, selection or reporter protein.

The invention provides for *C. reinhardtii* that produces recombinant AAV9, wherein the AAV9 comprises a heterologous protein for use as a viral vaccine or gene therapy vector. The invention also provides for a *C. reinhardtii* transformed with a polynucleotide construct comprising polynucleotide sequences to express the Rep78 protein, the Rep 52 protein, VP1 protein and the VP2/3 protein of AAV9 and comprises an AAV inverted terminal repeat (ITR) and 3' AAV ITR flanking the desired product sequence, and helper functions for generating a productive AAV infection, wherein the AAV9 is used as a viral vaccine or gene therapy vector. The viral vaccine or gene therapy vector comprise a heterologous polynucleotide sequence or expresses a heterologous protein sequence. In particular, the invention provides for *C. reinhardtii* transformed with a nucleotide construct comprising the nucleotide sequence of SEQ ID NO: 1, SEQ ID NO: 2, SEQ ID NO: 3 and/or SEQ ID NO: 4. The polynucleotide construct optionally comprises an AAV inverted terminal repeat (ITR) and 3' AAV ITR flanking the desired product sequence, and helper functions for generating a productive AAV infection, The invention also provides for cultures of any of the eukaryotic microalgae of the invention, wherein the eukaryotic microalgae stably expresses recombinant virus. For example, the invention provides for a culture of *C. reinhardtii* stably expressing AAV9.

In another aspect, the invention provides for methods of producing a recombinant virus, wherein the recombinant virus is a viral vaccine vector or a viral gene therapy vector, comprising the steps of growing an eukaryotic microalgae producing the recombinant virus. In any of the methods of the invention, the eukaryotic microalgae is transformed with a polynucleotide sequence expressing the recombinant virus. The polynucleotide sequence may be a heterologous polynucleotide sequence or a polynucleotide sequence that encodes a heterologous protein. The methods may optionally further comprise a step of purifying or recovering the recombinant virus. The microalgae may be transformed with a polynucleotide sequence or construct using the any technique known in the art such as microparticle bombardment, electroporation, glass beads, *Agrobacterium tumefaciens*, polyethylene glycol or silicon-carbide whiskers. In one embodiment, the microalgae is transformed with a polynucleotide construct comprising the polynucleotide sequence of SEQ ID NO: 1, SEQ ID NO: 2, SEQ ID NO: 3 and/or SEQ ID NO: 4.

The method of the invention are carried out with eukaryotic microalgae of the invention include green algae, diatoms, dinoflagellates and red algae. For example the microalgae of the invention are *Chlamydomonas* sp such as are *Chlamydomonas reinhardtii*, *Chlorella* sp such as *Chlorella vulgaris*, *Chlorella ellipsoidea*, *Chlorella sorokiniana* and *Chlorella kessleri*, *Volvox* sp. such as *Volvox carteri*, *Dunaliella* sp. such as *Dunaliella salina*, *Ostreococcus* sp. such as *Ostreococcus tauri*, *Phaeodactylum* sp. such as *Phaeodactylum tico* and *Phaeodactylum tricornutum*, *Gonium* sp. such as *Gonium pectoral*, *Cyanidiosschyzon* sp. such as *Cyanidiosschyzon merolae*, *Haematococcus* sp. such as *Haematococcus pluvialis*, *Porphyridium* spp., *Chlorarachniophytes*, *Lotharella* sp. such as *Lotharella amoebi-*

*formis* The eukaryotic microalgae of the invention are diatoms such as *Cyclotella cryptica, Navicula saprophila, Phaeodactylum tricornutum, Thalassiosira weissflogii, Cylindrotheca fusiformis* and *Chaetoceros* sp. The microalgae of the invention may be dinoflagellates such as *Amphidinium* or *Symbiodinium microadriaticum*. The microalgae of the invention are euglenoids such as *Euglena gracilis*. In a particular embodiment, the eukaryotic microalgae of the invention is *Chlamydomonas reinhardtii*.

Any of the methods of the invention may be carried out with eukaryotic microalgae that produce a recombinant virus that is a replication-restricted poxvirus, replication-restricted adenovirus, influenza virus, replication-incompetent alphavirus, parvovirus (e.g., AAV), adenovirus, retrovirus, lentivirus, attenuated flavivirus, or herpesvirus.

In a particular embodiment, the methods of the invention use an eukaryotic microalgae to produce recombinant adeno associated virus (rAAV). For example, the eukaryotic microalgae is transformed with a polynucleotide construct comprising a polynucleotide sequence encoding Rep 78 protein, Rep 52 protein, VP1 protein or VP2/3 protein, and the construct optionally further comprises an AAV inverted terminal repeat (ITR) and 3' AAV ITR flanking the desired product sequence, and optionally helper functions for generating a productive AAV infection. The eukaryotic microalgae is transformed with a polynucleotide construct comprising one or more polynucleotide sequences encoding Rep 78 protein, Rep 52 protein, VP1 protein and VP2/VP3 protein, and the construct optionally further comprises an AAV inverted terminal repeat (ITR) and 3' AAV ITR flanking the desired product sequence, and optionally helper functions for generating a productive AAV infection. In addition, the eukaryotic microalgae is transformed with a polynucleotide construct comprising one or more polynucleotide sequences encoding Rep 78 protein, Rep 52 protein, VP1 protein, VP2 protein and VP3 protein, and the construct optionally further comprises an AAV inverted terminal repeat (ITR) and 3' AAV ITR flanking the desired product sequence, and optionally helper functions for generating a productive AAV infection. The polynucleotide constructs that transform the eukaryotic microalgae of the invention may express VP2/VP3 protein under a single promoter or may express VP2 protein and VP3 protein under separate promoters. Alternatively, the eukaryotic microalgae is transformed with multiple polynucleotide constructs (one or more polynucleotide constructs), each comprising at least one polynucleotide sequence encoding Rep 78 protein, Rep 52 protein, VP1 protein, VP2/3 protein, VP2 protein or VP3 protein, and one or more of the polynucleotide constructs optionally further comprise an AAV inverted terminal repeat (ITR) and 3' AAV ITR flanking the desired product sequence, and helper functions for generating a productive AAV infection. For example, any of the methods utilizing a eukaryotic microalgae of the invention produce a recombinant virus that is AAV1, AAV2, AAV3, AAV4, AAV5, AAV6, AAV7, AAV8, AAV9, AAV10, AAV11, AAV12 or AAV13. In a particular embodiment, the methods of the invention utilize an eukaryotic microalgae produces a recombinant virus that is AAV9.

In any of the methods of the invention, the methods are carried out with an eukaryotic microalgae of the invention, wherein the microalgae is transformed with a polynucleotide construct comprising a nucleotide sequence encoding a heterologous protein such as a marker, selection or reporter protein.

DETAILED DESCRIPTION

Figure 1:
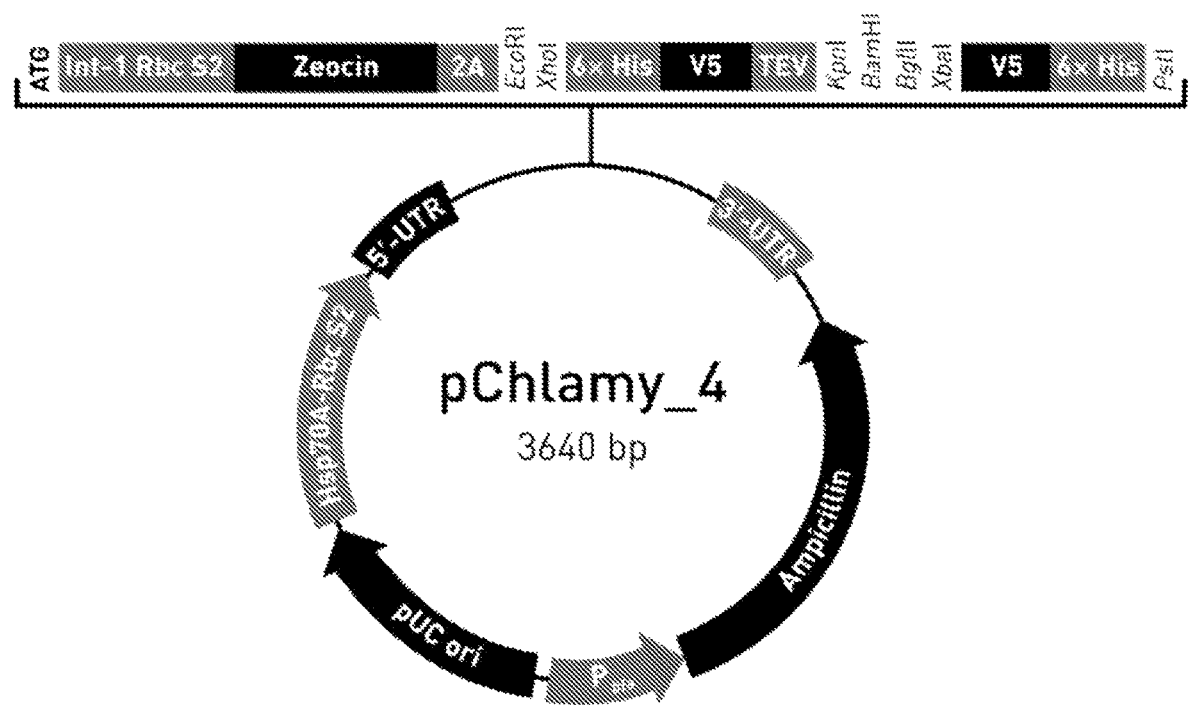
FIG. 1 provides a schematic of the pCHlamy 4 expression construct.

The present invention contemplates an eukaryotic microalgal system for producing recombinant viruses for use as gene therapy vectors or vaccine vectors. The recombinant viruses contemplated are not identical to any naturally-occurring virus. The advantages of the microalgal system include ease of culturing and maintenance, low production cost and simple purification process, rapid scalability to larger volumes and ability to support large scale viral replication and packaging.

Examples of eukaryotic microalgae which are especially well-suited for use in the production system include, but are not limited to, members of the *Chlamydomonas* species, particularly *Chlamydomonas reinhardtii* (*C. reinhardtii*), the *Chlorella* species (e.g., *Chlorella* sp.), the *Volvox* species (e.g., *Volvox carteri*), and some marine macrophytes. Other eukaryotic microalgae contemplated include, but are not limited to, *Dunaliella salina, Ostreococcus tauri, Phaeodactylum tico* and *Cyanidiosschyzon merolae*. See, Gong et al., J. Ind. Microbiol. Biotechnol., 38: 1879-1890 (2011). These eukaryotic microalgae species and additional species of microalgae that can be successfully transformed are provided in Table 1. The key features of these species are also provided in Table 1 (also summarized in Gong et al., which is incorporated by reference herein).

TABLE 1

| Microalgal species | Taxa | Key features related to genetic transformation |
|---|---|---|
| Chlamydomonas reinhardtii | Chlorophyta | Unicellular; cell-wall-deficient mutants; achievement of stable transformation of nuclear, chloroplast, and mitochondrial; diverse methods of transformation; GC-bias for nuclear gene |

TABLE 1-continued

| Microalgal species | Taxa | Key features related to genetic transformation |
|---|---|---|
| | | codons and AT-bias for chloroplast gene codons; extremely high GC content; available genome sequences and metabolic pathways |
| Chlorella sp. | Chlorophyta | Unicellular; small genome size; food supplement; fast growth rate; easy to culture; similar metabolic pathways to higher plants; often insensitive to certain antibiotics such as chloramphenicol and kanamycin |
| Dunaliella salina | Chlorophyta | Unicellular; resistant to high salinity; not easily contaminated by other organisms during mass culture; lack of a rigid polysaccharide cell wall; natural protoplast; not producing toxins and classified as a food source |
| Volvox carteri | Chlorophyta | Multicellular; closely related to unicellular Chlamydomonas reinhardtii; sequenced genome (approximately 138 Mb in size); composed of two cell types, somatic and reproductive; sexual development is initiated by a glycoprotein pheromone; |
| Ostreococcus tauri | Prasinophyta | Unicellular; minimal cellular organization; lacking flagella; the smallest living eukaryote compact and sequenced genome (12.56 Mb, one-tenth the size of Chlamydomonas) |
| Phaeodactylum tricornutum | Bacillariophyta | Multiple cell morphology; insensitive to most of the common antibiotics; well-established genetic systems; multiple marker genes available; diverse and advanced molecular toolkits; available genome sequences; routine transformation method; biased codon usage with a preference for G/C in the third position of the codon; GC content (48%) represents a typical value for eukaryotes |
| Cyanidioschyzon merolae | Rhodophyta | Unicellular; small genome size; available genome sequences; the cell contains a single nucleus, a single mitochondrion and a single chloroplast; unique chloroplast genome; resistant to extremely acid environment; simple life cycle; gene-targeting nuclear genome can be achieved by homologous recombination |

*C. reinhardtii* grow vegetatively through mitotic division of haploid cells. Haploid cells are of either the (−) or (+) mating type. When grown in the absence of nitrogen, haploid cells of opposite mating types associate, are held together through their flagella, and eventually fuse to form a diploid zygospore. The diploid zygote undergoes meiosis and releases four haploid cells that resume the vegetative life cycle. *C. reinhardtii* grows rapidly and is easily and inexpensively grown in culture. Exogenous DNA can easily be introduced into the nuclear, chloroplast, and mitochondrial genome of this algae, and can be expressed at high efficiency (e.g., 1% of total cellular protein). Auxotrophic mutants (mutants that differ from the wild-type in requiring one or more nutritional supplements for growth) are readily available at the *Chlamydomonas* Genetic Stock Center. One example of a walled green algae is *Chlamydomonas* strain CC-744. One example of a wall-less green algae is *Chlamydomonas* strain CC-425. Both of these strains are available from *Chlamydomonas* Genetic Stock Center, Duke University (Durham, N.C.). Additional strains include wild type CC-124, CC-125, CC-137 (commercially available from Invitrogen), CC-148, CC-198 and mutant strains CC-1852, CC-1213, CC-421, CC-1312, CC-1933, CC-1995 and CC-1996 (Gillham et al., Genetics 115: 677-684, 1987).

Another *C. reinhardtii* strain, DG8-108, was created by exposing wild-type *C. reinhardtii* 137-C to γ-radiation. DG8-108 cells may be range from 18-25 microns in length, are green in color (nearest color equivalent: Pantone #364), and have either a spherical and/or ovate morphology. DG8-108 reproduces vegetatively by longitudinal fission of the cells. DG8-108 can be cultivated and maintained in agar (plates) or liquid culture. DG8-108 cultivated and maintained on agar plates with mineral medium form green colonies (nearest color equivalent: Pantone #364) that are 0.3-0.5 cm in diameter within 10 days. The size of individual DG8-108 cells is 60 to 80% greater than wild-type varieties. The size of DG8-108 colonies in 1.3-1.8 times greater than the size of wild-type colonies. Adult cells of DG8-108 have a very large chloroplast that occupies nearly 2/3 of the total cell volume, and the chloroplast has 1.9-2.0 (SD=0.4) times more thylakoid membranes compared to wild-type cells. DG8-108 growth rate may be increased by increasing the concentration of medium salts by 5 times compared to normal growth medium. Its doubling time can be decreased from 10-12 hours to 6 hours.

In one aspect, the disclosure provides an eukaryotic microalgae that produces a recombinant virus. In some embodiments, the recombinant virus is recombinant vaccine vector including, but not limited to, a replication-restricted poxvirus (e.g., MVA, NYVAC, FP9, TROVAC and ALVAC strains), replication-restricted adenovirus (e.g., replication-restricted Ad5 and ONYX-015), influenza virus, replication-incompetent alphavirus [e.g., Venezuelan equine encephalitis virus (VEE), Sindbis virus (SIN), Semliki forest virus (SFV) and VEE-SIN chimeras, parvovirus (e.g., AAV), lentivirus, attenuated flavivirus, or herpesvirus. In some embodiments, the recombinant virus is a recombinant gene therapy vector including, but not limited to, a parvovirus (e.g., AAV), adenovirus (e.g., Ad5 and ONYX-015), retrovirus or herpes simplex virus.

In some embodiments, the eukaryotic microalgae is *C. reinhardtii*.

The eukaryotic microalgae are genetically engineered to comprise the components needed for assembly of the recombinant virus in the eukaryotic microalgae. As will be understood by those skilled in the art, the eukaryotic microalgae thus comprise a recombinant viral genome comprising one or more polynucleotides of interest (e.g., encoding an immunogen, a therapeutic gene product, an inhibitory RNA or a therapeutic RNA), viral structural components, any viral non-structural components and any necessary helper virus components/functions.

In some embodiments, the recombinant viral genomes are rAAV genomes. The rAAV genomes comprise one or more AAV ITRs flanking a heterologous polynucleotide of interest. If the polynucleotide of interest is to be transcribed it is operatively linked to transcriptional control DNA, specifically promoter DNA and polyadenylation signal sequence DNA that are functional in target cells to form a gene cassette. The gene cassette may also include intron sequences to facilitate processing of an RNA transcript when expressed in mammalian cells. Alternatively, the polynucleotide in the rAAV genome be an inhibitor RNA. The inhibitor RNAs may be antisense RNAs, ribozymes, small interfering RNAs (RNAi), miRNA or aptamers. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.).

The rAAV genomes of the invention lack AAV rep and cap DNA. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12 and AAV-13. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); the AAV-11 genome is provided in Virology, 330(2): 375-383 (2004), the genome of AAV-12 is provided in GenBank Accession No. DQ813647.1, and the genome of AAV-13 is provided in GenBank Accession No. EU285562.1.

In another aspect, the invention provides one or more DNA plasmids comprising viral genomes of the invention, encoding viral structural or non-structural components and encoding helper virus proteins. The DNA plasmid(s) is(are) transferred to eukaryotic microalgae for assembly of the viral genome into infectious viral particles. As one example, techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions (e.g., adenovirus, E1-deleted adenovirus or herpesvirus helper virus functions). The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12 and AAV-13. Production of pseudotyped rAAV is disclosed in, for example, WO 01/83692. Other types of rAAV variants, for example rAAV with capsid mutations, are also contemplated. See, for example, Marsic et al., Molecular Therapy, 22(11): 1900-1909 (2014).

Methods are provided for generating a packaging cell to create a eukaryotic microalgae that contains all the necessary components for recombinant virus particle production such as rAAV production. For example, a rAAV genome lacking AAV rep and cap genes, and AAV rep and cap genes separate from the rAAV genome, are introduced into the eukaryotic microalgae. The eukaryotic microalgae are also provided with AAV helper virus functions (e.g., from adenovirus, herpes simplex virus or vaccinia virus). In some embodiments, the components necessary for recombinant virus particle production are transiently introduced into eukaryotic microalgal packaging cells. In other embodiments, packaging cells stably comprise one, some or all of the necessary components for recombinant virus particle production, and any other components are provided transiently.

General principles of rAAV production are reviewed in, for example, Carter, Current Opinions in Biotechnology, 1533-1539 (1992); and Muzyczka, Curr. Topics in Microbial. and Immunol., 158:97-129 (1992). Various approaches are described in Ratschin et al., Mol. Cell. Biol, 4:2072 (1984); Hermonat et al., Proc. Natl. Acad. Sci. USA, 81:6466 (1984); Tratschin et al., Mol. Cell. Biol, 5:3251 (1985); McLaughlin et al., J. Virol., 62:1963 (1988); and Lebkowski et al., Mol. Cell. Biol., 7:349 (1988). Samulski et al., J. Virol., 63:3822-3828 (1989); U.S. Pat. No. 5,173, 414; WO 95/13365 and corresponding U.S. Pat. No. 5,658, 776; WO 95/13392; WO 96/17947; PCT/US98/18600; WO 97/09441 (PCT/US96/14423); WO 97/08298 (PCT/US96/ 13872); WO 97/21825 (PCT/US96/20777); WO 97/06243 (PCT/FR96/01064); WO 99/11764; Perrin et al., Vaccine, 13:1244-1250 (1995); Paul et al., Human Gene Therapy, 4:609-615 (1993); Clark et al., Gene Therapy, 3:1124-1132; U.S. Pat. Nos. 5,786,211; 5,871,982; and 6,258,595. It is contemplated that the AAV production components used in these approaches can be adapted for recombinant virus production in eukaryotic microalgal cells. Similarly, it is contemplated that production components known in the art for production of other recombinant viruses can be used or adapted as described herein to produce the recombinant viruses in eukaryotic microalgae.

The expression of viral structural components, viral non-structural components and helper virus proteins is controlled by regulatory sequences (e.g., promoters, enhancers and transcription terminators) which regulate transcription in the nucleus, chloroplast, or mitochondria, of the eukaryotic microalgae. In some embodiments, the promoter is a promoter endogenous to the eukaryotic microalgae, i.e., it directs transcription of genes that are normally present in the algae. Examples of suitable promoters for *C. reinhardtii* include, but are not limited to, the chloroplast gene promoter psbA and the nuclear promoter region of the β2 tubulin gene. Other examples of promoters are hsp70 ("heat shock protein" promoter), rbcS ("rubisco small subunit" promoter) and tubA2 ("actin" promoter) promoters. In some embodiments, the promoter is an inducible promoter that can be used to regulate the timing and relative level of expression of viral components (e.g., AAV rep/cap genes). Examples of enhancers are the tubA2 intron 1, the HSP70 enhancer and the rcbS2 intron 1. Additional promoters are set out in Table 2 (see also Gong et al. Ind. Microbiol. Biotechnol., 38: 1879-1890 (2011), incorporated by reference herein).

TABLE 2

| Promoter of gene and its product | Source | Host species of microalgae |
|---|---|---|
| RbcS2, rubisco small subuit 2 | *Chlamydomonas* | *Chlamydomonas* |
| Fcp, fucoxanthin chlorophyll-a or -c binding protein | *Phaeodactylum tricornutum*, *Thalassiosira pseudonana* | *P. tricornutum*, *Chaetoceros* sp. |
| Hsp70, heat shock protein 70 | *Chlamydomonas* | *Chlamydomonas* |
| 35S, cauliflower mosaic virus 35S | Cauliflower mosaic virus | *Chlamydomonas*, *Amphidinium*, and *Symbiodinium* |
| Nos, nopaline synthase | *Agrobacterium tumefaciens* | *Chlamydomonas*, *Amphidinium*, and *Symbiodinium* |
| NR, nitrate reductase | *Thalassiosira pseudonana* | *Chaetoceros* sp. |
| PsaD, photosystem I complex protein | *Chlamydomonas* | *Chlamydomonas* |

In some embodiments, the polynucleotide sequences of viral structural components, the polynucleotide sequences of viral non-structural components and the polynucleotide sequences of helper virus proteins that are introduced into the eukaryotic microalgae are codon-optimized for expression in the eukaryotic microalgae. See, the nuclear codon usage of *C. reinhardtii* according to the table provided by the Kazusa Codon Usage Database (Species ID: 3055), which can be used with, for example, Gene Designer software from DNA 20 to generate a codon-optimized polynucleotide sequence. Codon optimized nucleotide sequence encoding Rep 78 is set out as SEQ ID NO: 1. Codon optimized nucleotide sequence encoding Rep 52 is set out as SEQ ID NO: 2. Codon optimized nucleotide sequence encoding VP1 is set out as SEQ ID NO: 3. Codon optimized nucleotide sequence encoding VP2/3 is set out as SEQ ID NO: 4.

Polynucleotides comprising recombinant viral genomes, polynucleotides encoding viral structural components, polynucleotides encoding viral non-structural components and polynucleotides encoding helper virus proteins are stably or transiently introduced into the eukaryotic algae by standard transformation methods known to those skilled in the art, such as electroporation, vortexing cells in the presence of exogenous DNA, acid washed beads, polyethylene glycol, plasmid conjugation and microparticle bombandment. See, for example, Hallmann, Transgenic Plant Journal, 1:81-98 (2007). The transformed algae are recovered on a solid nutrient media or in liquid media. See also, Harris, Annual Review of Plant Physiology and Plant Molecular Biology 52:363-406 (2001) and EMBO Practical Course: Molecular Genetics of *Chlamydomonas*, Laboratory protocols. Geneva, Sep. 18-28, 2006. See also, Gong et al., Ind. Microbiol. Biotechnol., 38: 1879-1890 (2011).

Exemplary microalgal species that can be transformed are summarized in Table 3 (see also, Gong et al., Ind. Microbiol. Biotechnol., 38: 1879-1890 (2011) which is incorporated by reference herein).

TABLE 3

| Species | Transformation method | Genome |
|---|---|---|
| *C. reinhardtii* | Microprojectile bombardment | Nuclear |
| | Electroporation | Nuclear |
| | Glass bead | Nuclear |
| | *Agrobacterium tumefaciens* | Nuclear |
| | Microprojectile | Chloroplast |
| | Microprojectile | Mitochondrial |
| *Dunaliella salina* | Electroporation | Nuclear |
| *Chlorella ellipsoidea* | Polyethylene glycol | Nuclear |
| *Chlorella sorokiniana* | Microprojectile bombardment | Nuclear |
| *Chlorella vulgaris* | Electroporation | Nuclear |
| *Chlorella kessleri* | Microprojectile bombardment | Nuclear |
| *Haematococcus pluvialis* | Microprojectile bombardment | Nuclear |
| *Ostreococcus tauri* | Electroporation | Nuclear |
| *Gonium pectorale* | Microprojectile bombardment | Nuclear |
| *Volvox carteri* | Microprojectile bombardment | Nuclear |
| *Cyclotella cryptica* | Microprojectile bombardment | Nuclear |
| *Navicula saprophila* | Microprojectile bombardment | Nuclear |
| *Phaeodactylum tricornutum* | Microprojectile bombardment | Nuclear |
| *Thalassiosira weissflogii* | Microparticle bombardment | Nuclear |
| *Cylindrotheca fusiformis* | Microprojectile bombardment | Nuclear |
| *Chaetoceros* sp. | Microparticle bombardment | Nuclear |
| *Amphidinium* | Silicon carbide whiskers | Nuclear |
| *Symbiodinium microadriaticum* | Silicon carbide whiskers | Nuclear |
| *Cyanidioschyzon merolae* | Electroporation | Nucleus |
| *Porphyridium* spp. | Microprojectile bombardment | Chloroplast |
| *Lotharella amoebiformis* | Microparticle bombardment | Nuclear |
| *Euglena gracilis* | Microprojectile bombardment | Chloroplast |

In some embodiments, a plasmid capable of integrating polynucleotides into a chromosome of the algae is used. There are a large numbers of vectors known and characterized. One example is pSP124 described in Lumbreras et al., The Plant Journal 14(4):441-447 (1998). Another plasmid vector integrates into the nucleus of algal cells and expresses its proteins which are localized to the cytoplasm of algal cells. One particular vector of this type is pSSCR7, derived from a the plasmid described in Davies et al. Plant Cell, 6:53-63 (1994). Another type of vector also integrates into the nucleus but expresses proteins that are localized to the periplasm. One particular vector of this type is a derivative of pSSCR7 which has a 5' aryl sulfatase periplasmic targeting transit sequence (Davies et al., Plant Cell, 6:53-63 (1994)).

Another exemplary plasmid vector is pChlamy 4 (commercially available from Thermo Fisher Scientific). pChlamy 4 vector is designed to express proteins as transcriptional fusions with the bleomycin/zeocin resistance gene sh-ble (Rasala et al., 2012). The self-cleaving sequence for the 2 A peptide from the foot-and-mouth disease virus (FMDV) is placed between the antibiotic resistance gene and the gene of interest. It encodes a short ~20 amino acid sequence that mediates proper cleavage to yield two discrete proteins.

In some embodiments, a plasmid that integrates into the chloroplast genome by homologous recombination and expresses proteins that are localized to the chloroplasts is used (Hutchinson et al., Chapter 9, Chloroplast transformation, pages 180-196 in Molecular Genetics of Photosynthesis, Frontiers in Molecular Biology. Anderson B., Salter A H, and Barber J. Eds.: Oxford University Press (1996)).

With respect to the plasmids that express in specific compartment of the algae, localization sequences are used that allow expression of the transcript in one compartment but then target the protein to the correct compartment post-transcription. (Rasala et al, 2014: enhanced genetic tools for engineering multigene traits into green algae. PLoS One 9(4):e94028.

In some embodiments, to increase growth rate and chlorophyll production, the eukaryotic microalgae include one or more expressible genetic constructs capable of driving the expression of one or more polynucleotides encoding glutamine phenylpyruvate transaminase (GPT), and in some embodiments, one or more polynucleotides encoding glutamine synthetase and GPT.

In some embodiments, the eukaryotic microalgae have partially suppressed ribulose-1,5-bisphosphate carboxylase/oxygenase (RUBISCO) enzyme achieved by standard molecular biological procedures such as by antisense or RNAi technology.

In some embodiments, a gene silencing inhibitor is also introduced into the eukaryotic microalgae. A gene silencing inhibitor is a peptide that induces relaxation of nucleosomes in the algae's nucleus. Gene silencing inhibitors include histone acetyl transferases (HATs) and other peptides that modify elements of the nucleosome, causing the chromatin structure to relax and to allow transcription factors to access the gene of interest. HAT proteins and the HAT domains of p300 and of other HAT proteins are known to cause histone acetylation and can be utilized in the invention. Fusion peptides that increase expression of the transgene may also be incorporated such as FMDV 2 A peptide fused to the transgene and a resistance marker like sh-ble. This plasmid vector available from Invitrogen is what we have been using so far. In accordance to the invention, the domain responsible for the acetylation activity or the whole protein is deployed. See Fukuda et al., Brief Funct. Genomic Proteomic, 5(3):190-208 (2006); Renthal and Nestler, Semin Cell Dev Biol. 20(4):387-394 (Epub 2009); and Lin et al., Genes Dev., 22(15):2062-2074 (2008). In some embodiments, a p300 protein is used as a gene silencing inhibitor. In some embodiments, a *Chlamydomonas*-derived p300 protein or HAT domain of a *Chlamydomonas*-derived p300 protein is utilized.

In some embodiments, the gene silencing inhibitor is functionally tethered or, preferably, fused to a DNA binding protein or domain thereof. The DNA binding protein or domain binds to a particular DNA sequence, bringing the gene silencing inhibitor to its histone target at a location in the vicinity of the binding site and thereby inducing relaxation of the nucleosome at that genetic location. As the nucleosome relaxes, the nearby DNA sequence is exposed to transcription factors and is more actively transcribed. Examples of proteins targeting specific DNA motifs applicable to this invention include the Gal4 protein and Early Growth Response Protein 1. DNA binding site motifs for these proteins are known. Likewise, the binding domains of these as well as the LexA protein are known and are preferentially used, instead of the full-length protein. See for example Young, Biol. Reprod., 58:302-311 (1998) and Joung et al., Proc. Natl. Acad. Sci., 97:7382-7387 (2000). LexA is a gene of bacterial origin. LexA proteins or genes are not known in algae. Thus, it is unlikely that the *Chla-*

*mydomonas* genome will contain the DNA binding sequence of LexA. The function of LexA in the context of the invention is to bind a particular DNA sequence LexA binding sites are found upstream promoters in a number of microorganisms. The binding domain of the LexA protein is known and, for the purpose of the invention, it is preferred to employ only the binding domain (Protein ID: 2293118 from NCBI Database).

In some embodiments, the activity of proteases, such as ATP-dependent proteases, is limited in the eukaryotic algae.

In some embodiment, a selection marker or resistance marker is also introduced into the eukaryotic microalgae. These markers act as reporters for viral protein expression. Exemplary selection and/or resistance markers are provided in Table 4 (see also Greistbeck et al., Mol. Biotechnol. 34(2):213-23, 2006. Selection markers that are particularly useful for *C. reinhardtii* are provided in Table 5. Reporter genes that are particularly useful in *C. reinhardtii* are provided in Table 6.

TABLE 4

| Marker or reporter | Coding protein or product | Gene source |
|---|---|---|
| AphVIII | Aminoglycoside 3' phosphotransferase, resistance to paromomycin, kanamycin, and neomycin | *Streptomyces rimosus* |
| Ble | Bleomycin resistance protein, resistance to tallysomycin and related antibiotics | *Streptoalloteichus hindustanus* |
| Cat | Chloramphenicol acetyltransferase, resistance to chloramphenicol | Transposon Tn9 |
| nptII | Neomycin phosphotransferase II, resistance to G418 | *E.coli* transposon Tn5 |
| aadA | Adenylyltransferase, resistance to spectinomycin | Eubacteria |
| Hpt | Hygromycin B phosphotransferase | *E. coli* |
| ChGfp | Modified green fluorescent protein, adapted to *Chlamydomonas* codon usage, reporter in *Chlamydomonas* | Synthetic |
| eGfp | Modified green fluorescent protein, adapted to human codon usage, reporter in *P. tricornutum* | Synthetic |
| Gus/uidA | β-Glucuronidase, reporter in *Amphidinium* and *Symbiodinium* | *E. coli* |
| Hup1 | Hexose transporter, marker or reporter in *P. tricornutum* and *Cylindrotheca fusiformis* | *Chlorella kessleri* |
| Luc | Luciferase, reporter in *P. tricornutum* and *Gonium pectorale* | *Hotaria parvula* |

TABLE 5

| Marker | Genome | Description |
|---|---|---|
| Arg 7 | nuclear | Arginino succinate lyase, arginine prototrophy, applicable only for arg7- strains |
| Nia1 (Nit1) | nuclear | Nitrate reductase, growth on nitrate as the sole nitrogen source, applicable only for nit1- strains |
| Nic7 | nuclear | Quinolinate synthetase A, growth without nicotinamide, applicable only for nic7- strains |
| Thi10 | nuclear | Hydroxyethylthiazole kinase, growth without thiamine, applicable only for thi10- strains |
| Cry1-1 | nuclear | Mutated rps14 gene (L153P) encoding the ribosomal protein S14, resistance to cryptopleurine/emetine |
| Ppx1 | nuclear | Mutated protoporphyrinogen oxidase (V389M), resistance to porphyric herbicides like S-23142 |
| als | nuclear | Mutated acetolactate synthase (K257T), resistance to sulfometuron methyl |
| ble | nuclear | Phleomycin from *Streptoalloteichus hindustanus*, resistance to zeocin |
| Aph7" | nuclear | Aminoglycoside phosphotransferase from *Streptomyces hygroscopicus*, resistance to hygromycin B |

TABLE 5-continued

| Marker | Genome | Description |
|---|---|---|
| aphVIII | nuclear | Aminoglycoside phosphotransferase from *Streptomyces rimosus*, resistance to paromomycin/kanamycin |
| aadA | Chloroplast (nuclear) | Eubacterial aminoglycoside adenine transferase, resistance to spectinomycin/streptomycin |
| aphA-6 | Chloroplast | Aminoglycoside phosphotransferase from *Acinetobacter baumannii*, resistance to kanamycin/amikacin |

TABLE 6

| Repoerter | Genome | Description |
|---|---|---|
| Ars | Nuclear | Arylsulfatase, for colorimetric assays, not under sulfur starvation |
| crgfp | Nuclear | Nuclear codon-optimized green fluorescent protein from *Aequorea victoria* |
| crluc | Nuclear | Nuclear codon-optimized luciferase from *Renilla reniformis* |
| gfpXt | Chloroplast | Chloroplast codon-optimized green fluorescent protein from *A. victoria* |
| rluc | Chloroplast | Luciferase from *R. reniformis* |
| luxCt | Chloroplast | Chloroplast codon-optimized luciferase luxAB from *Vibrio harveyi* |
| lucCp | Chloroplast | Chloroplast codon-optimized firefly luciferase |

In another aspect, methods of producing recombinant virus are provided. The methods comprise growing a eukaryotic microalgae producing the recombinant virus. In some embodiments the methods further comprise purifying or recovering the recombinant virus. In some embodiments, the recombinant virus is a viral vaccine vector. In some embodiments, the recombinant virus is a viral gene therapy vector.

Eukaryotic microalgae can be lysed with a hydrophilic ionic liquid in a lysing reactor. See, for example, U.S. Pat. No. 8,211,307.

The recombinant virus produced by the eukaryotic microalgae may be purified by methods standard in the art. For example, rAAV may be purified by methods standard in the art such as by column chromatography or cesium chloride gradients.

EXAMPLES

The invention will be more fully understood by reference to the following examples which detail exemplary embodiments of the invention.

Example 1

Design and Construction of rAAV9 Expression Plasmids

Production of AAV requires a set of components acting in trans with respect to the vector genome. These include AAV non-structural proteins expressed from rep genes. Rep78, Rep68 are derived from p5 promoter transcript while Rep52, Rep40 are derived from an internal p19 promoter transcript. All four Rep proteins are not necessary for AAV production; Rep78 and Rep52 are sufficient. AAV structural proteins VP1, VP2 and VP3 are encoded by cap genes and expressed as a single transcript. The present example describes production of functional AAV9 caspids but this may be carried out for any AAV serotype.

A rAAV vector genome comprises an expression cassette of a polynucleotide of interest (e.g., a therapeutic gene), flanked by Inverted Terminal Repeats (ITRs). These are the only cis elements required for replication and packaging of the polynucleotide of interest within the final AAV capsid. In order to express both nonstructural and structural proteins efficiently in *C. reinhardtii*, algal codon-optimized DNA sequences of Rep and Cap genes are cloned into *Chlamydomonas* expression vectors under constitutively active promoters Hsp70, RbcS2 and PsaD along with algal selection markers. Non-coding elements like 5' UTRs, introns and 3' UTRs are also incorporated in the expression cassettes to achieve higher protein expression. AAV-CB-therapeutic gene plasmid with the therapeutic gene under Chicken β-Actin promoter (CB), flanked by AAV ITRs is utilized as the vector genome. A vector genome encoding green fluorescent protein can be used as a control genome.

Production of functional AAV9 capsids is dependent on Replication (Rep) and Capsid (Cap) genes. Rep genes are required for the replication of the viral genome while Capsid genes are important for the production of AAV9 capsids as well as packaging of the viral genomes within the capsids. Historically, as human cells have been utilized to produce these viral particles, no additional sequence modification is required while expressing these genes in human cells. However, to achieve efficient expression in microalgal cells, DNA sequences of Rep and Cap genes were first optimized for algal codon usage utilizing the codon optimizer. Rep gene encodes for Rep78 and Rep 52 while Cap gene encodes for VP1, VP2 and VP3. Individual sequences for Rep 78 (SEQ ID NO: 1), Rep 52 (SEQ ID NO: 2), VP1 (SEQ ID NO: 3) and VP2/3 (SEQ ID NO: 4) were codon optimized and commercially synthesized from Genscript.

Figure 2:
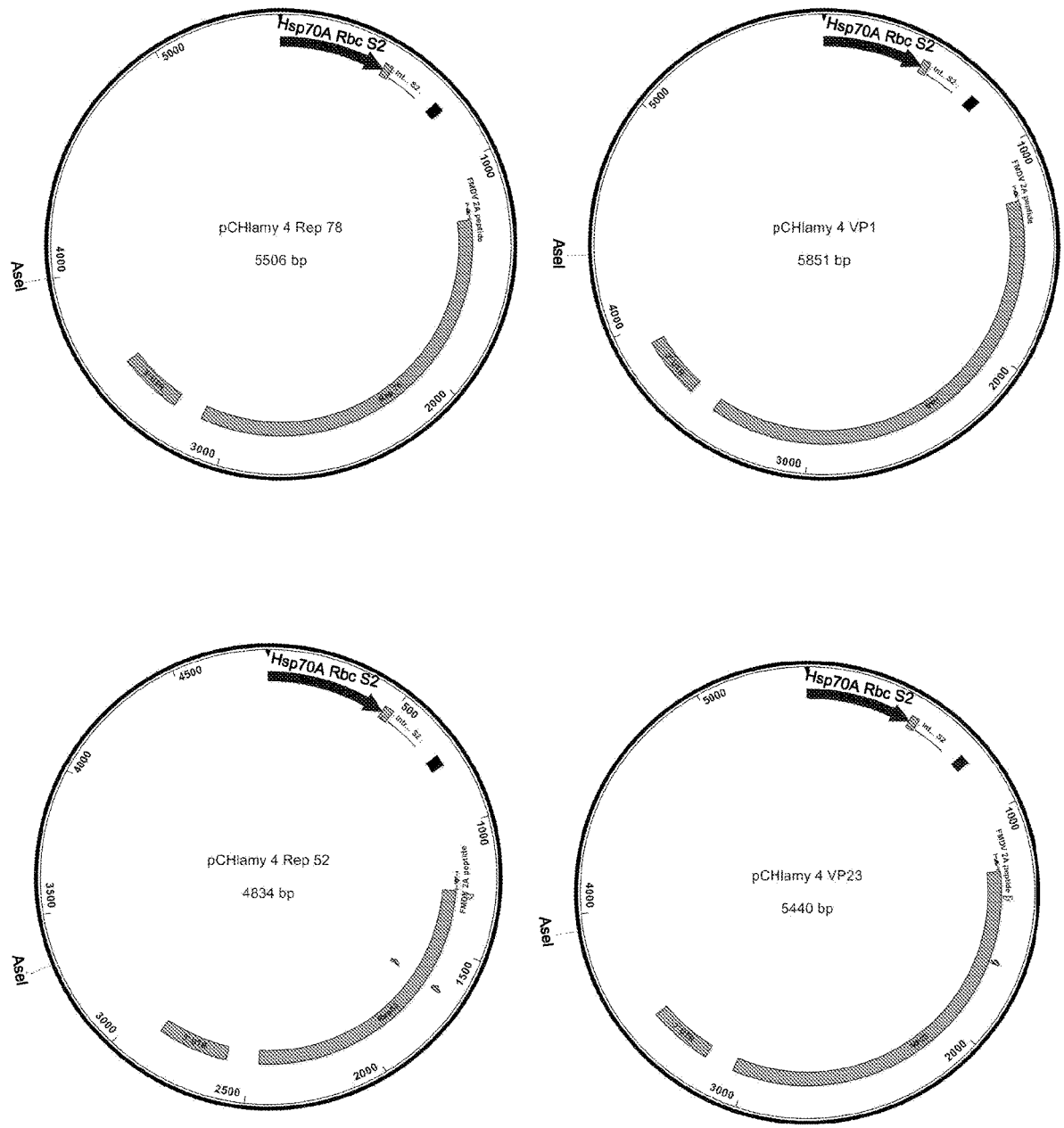
FIG. 2 provides a plasmid map of pChlamy 4 with single expression cassettes of Rep78, Rep52, VP1 and VP2/3.

In mammalian cells, single Rep gene can encode for both Rep78 and Rep 52 while single Cap gene encodes for VP1, VP2 and VP3. These multiple gene products are produced from the single stretch of DNA sequence with the help of internal promoters. However, as these promoters are only functional in mammalian cells, these multiple gene products need to be individually expressed in microalgal cells. To achieve this, codon optimized constructs of Rep78 (SEQ ID NO: 1), Rep52 (SEQ ID NO: 2), VP1 (SEQ ID NO: 3) and VP2/3 (SEQ ID NO: 4) were then cloned into algal expression plasmid kit obtained from Invitrogen. pCHlamy 4 expression construct, shown in FIG. 1, was utilized for its better expression and reduced genetic silencing of the transgene cloned into it. Plasmid maps of pChlamy 4 with single expression cassettes of Rep78, Rep52, VP1 and VP2/3 are set out in FIG. 2.

Figure 3:
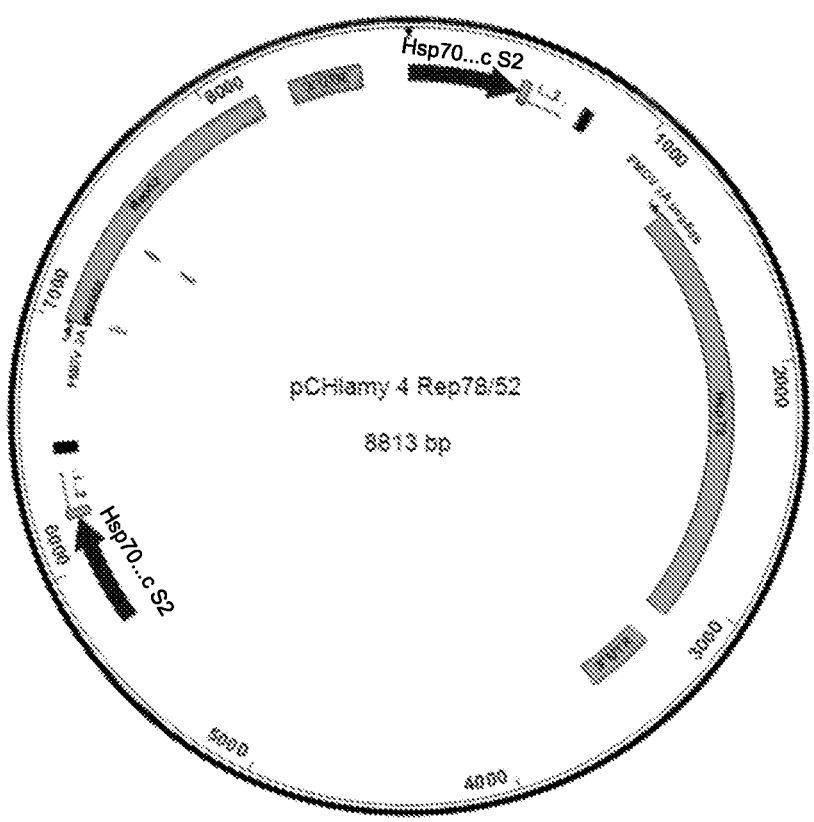
FIG. 3 provides plasmid maps of pChlamy 4 with dual expression cassettes of Rep78/52 and VP1/2/3.
Figure 3:
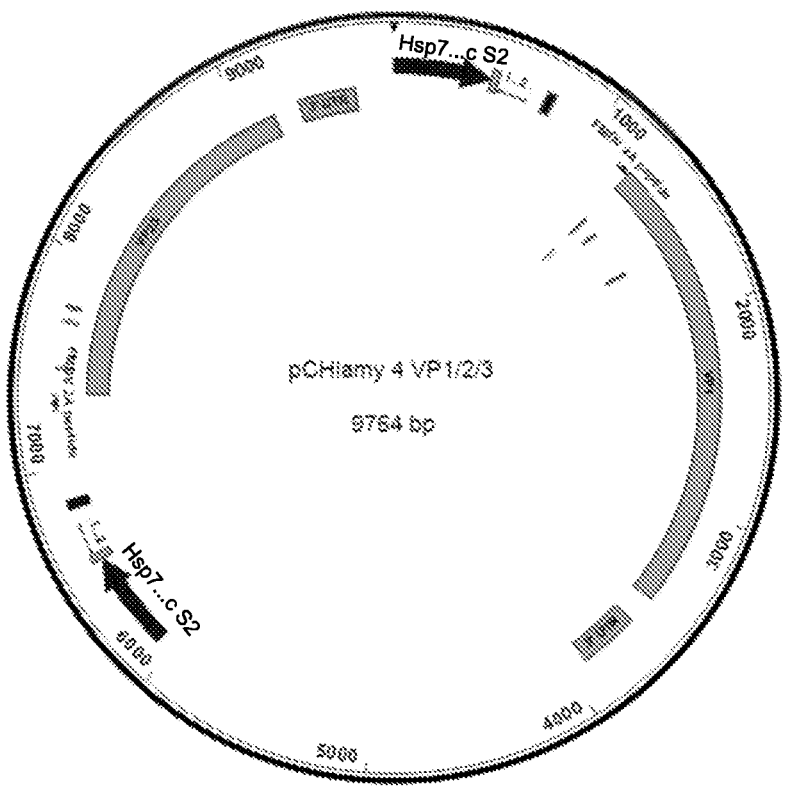

In order to minimize the further transformation steps, expression cassettes containing Rep 78 and Rep52 were combined together. Similarly, expression cassettes for VP1 and VP2/3 were also combined. Hence, in the final vectors, each transgene had its individual promoter for the highest expression. Plasmid maps of pChlamy 4 with dual expression cassettes of Rep78/52 and VP1/2/3 are set out in FIG. 3.

Example 2

Production of *C. reinhardtii* Line Expressing AAV Rep/Cap Proteins

Figure 4A:
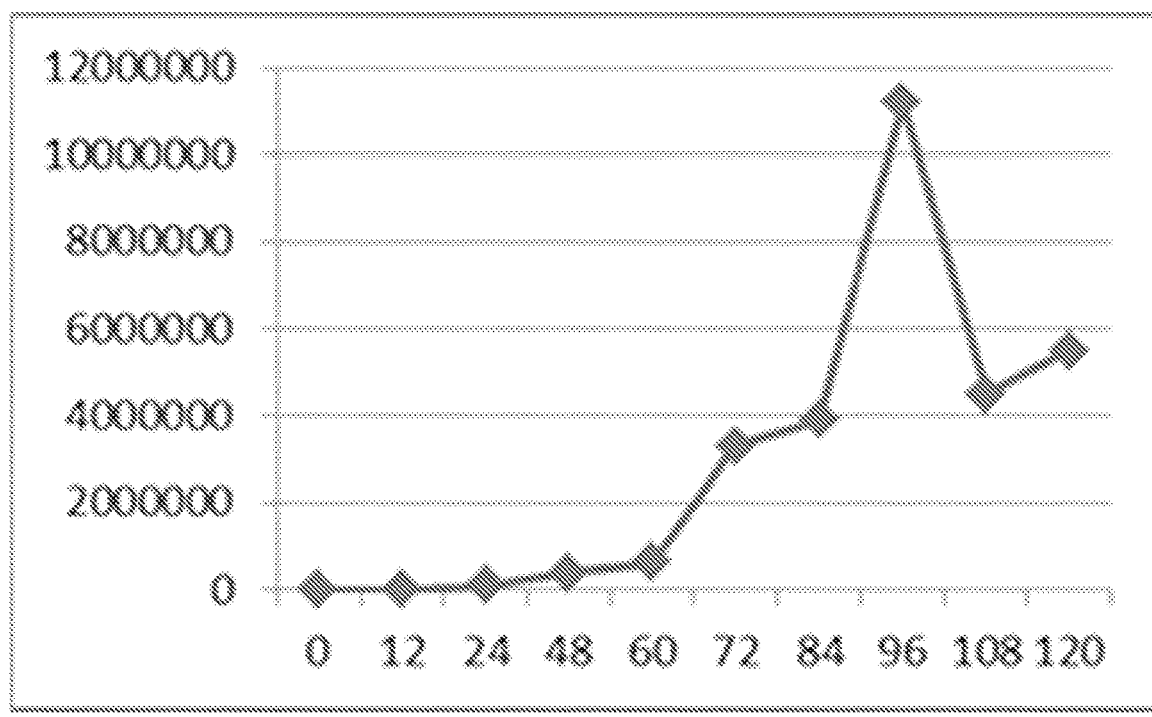
FIGS. 4A and 4B provide the growth rate and the doubling time of the *C. reinhardtii* cells used to express AAV rep/cap proteins.
Figure 4B:
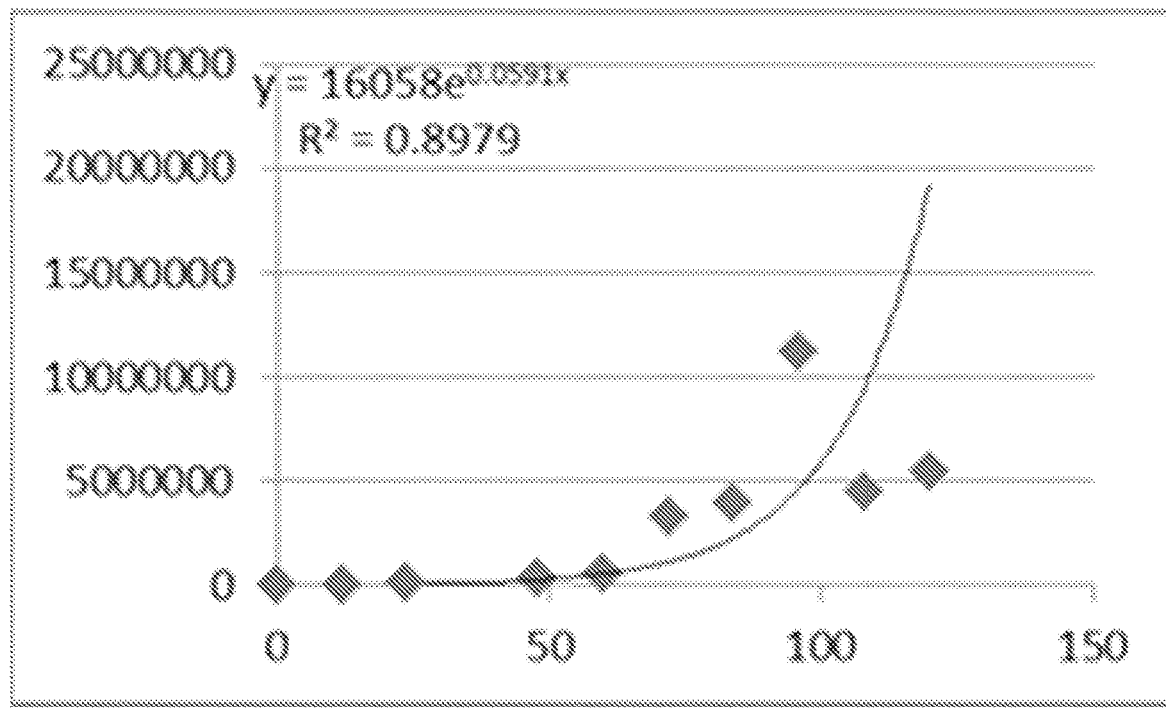

To generate the microalgae expressing AAV rep/cap proteins, *C. reinhardtii* cells (CC 137; commercially available from Invitrogen) were used as the host system. *C. reinhardtii* cells were purchased from Invitrogen and the cultures were established using Tris-Acetate Phosphate (TAP) liquid growth medium under constant illumination of 50 µE m-2 s-1 at 25° C. and 110 RPM. The growth rate of the *C. reinhardtii* line was 0.0591 and the doubling time was 11.72 hours (see FIG. 4).

Figure 5:
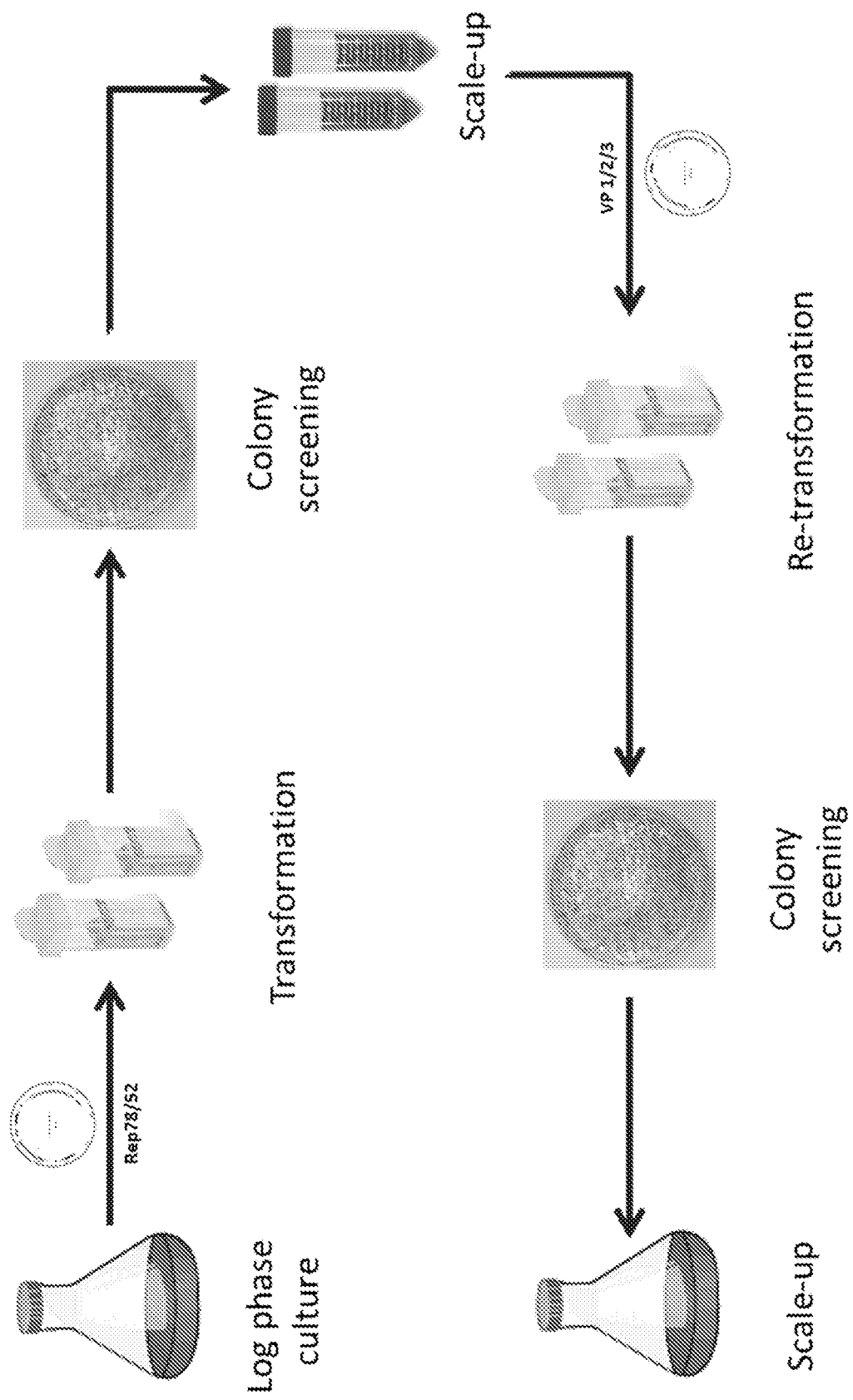
FIG. 5 provides the workflow for a sequential gene stacking approach to generate *C. reinhardtii* cells stable expressing Rep78/52 and VP1/2/3.
Figure 6:
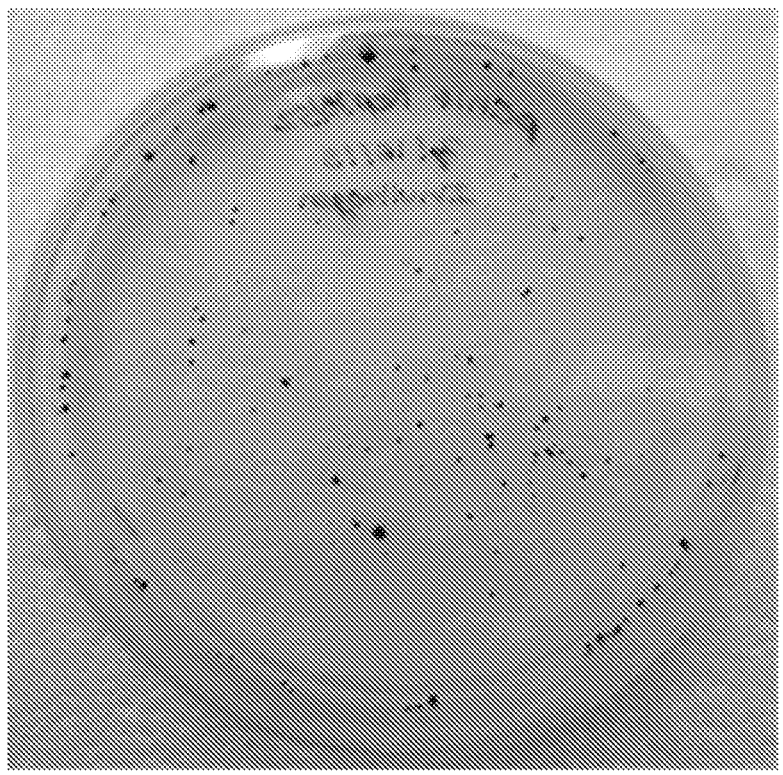
FIG. 6 depicts Positive clones of *C. reinhardtii* cells after transformation with Rep78/52 or VP1/2/3.
Figure 6:
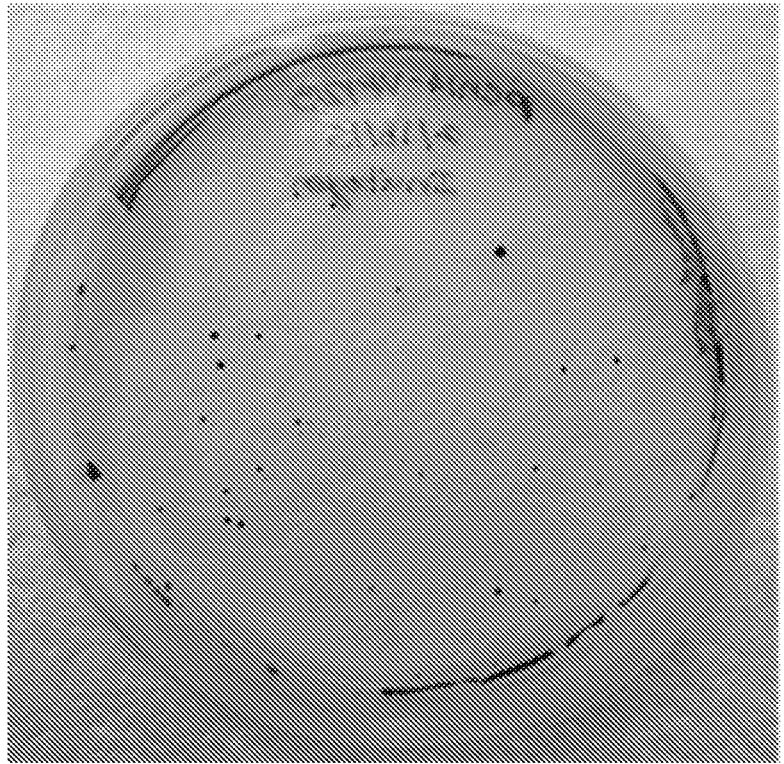

A sequential gene stacking approach was utilized to generate the stable lines of *C. reinhardtii* cells expressing AAV Rep/Cap proteins (FIG. 5). In this case, *C. reinhardtii* cells stably expressing Rep78/52 or VP1/2/3 were generated and then the same line is further transformed with the other Cap or Rep constructs. *C. reinhardtii* cells were transformed with Rep78/52 and VP1/2/3 plasmids individually via electroporation. Electroporation parameters used were as follows: Voltage 500V, Capacity 50 µF, Resistance 800Ω. The electroporated cells were further plated on TAP-Zeocin agar plates and incubated under constant illumination of 50 µE m-2 s-1 at 25° C. Exemplary positive clones of *C. reinhardtii* cell after transformation with Rep 78/52 or VP1/2/3 are shown in FIG. 6.

Transformation of *C. reinhardtii* cells with the plasmids DNA results in the integration of the DNA molecule in the nuclear genome. This allows the generation of stable cell line expressing the desired transgene or product. Nuclear integration of the plasmid will be confirmed with the help of colony PCR of the genomic DNA. After establishment of *C. reinhardtii* lines stably expressing either Rep or Cap genes, these cells are further transformed with the complementary plasmids by sequential transformation to obtain the *C. reinhardtii* cells expressing both Rep and Cap genes. Transformants are obtained on selective media plates and analyzed for the presence of all the plasmids by PCR.

To reduce the number of steps required to obtain the final desired microalgal transformant stably expressing all the Rep and Cap genes in optimal stoichiometric amounts, different combinations of the plasmids containing different promoters, resistance markers as well as mono or polycistronic mRNAs are utilized.

For example, *C. reinhardtii* cells were transformed with Rep78/52 and VP1/2/3 plasmids individually via electroporation. Electroporation parameters used were as follows: The electroporated cells were further plated on TAP-Zeocin agar plates and incubated under constant illumination of 50 µE m-2 s-1 at 25° C. Exemplary positive clones of *C. reinhardtii* cell after transformation with Rep 78/52 or VP1/2/3 are shown in FIG. 6.

Electroporation of *C. reinhardtii* cells with the plasmids DNA results in the integration of the DNA molecule in the nuclear genome. This allows the generation of stable cell line expressing the desired transgene or product. Nuclear integration of the plasmid were confirmed with the help of colony PCR of the genomic DNA.

Figure 7:
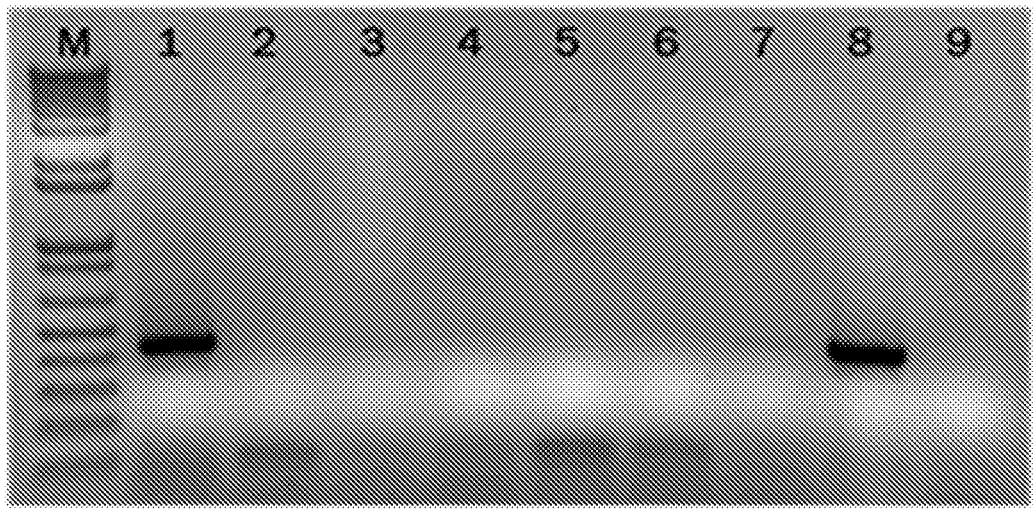
FIG. 7 demonstrates colony screening for Rep78/52 and VP1/2/3 clones.
Figure 7:
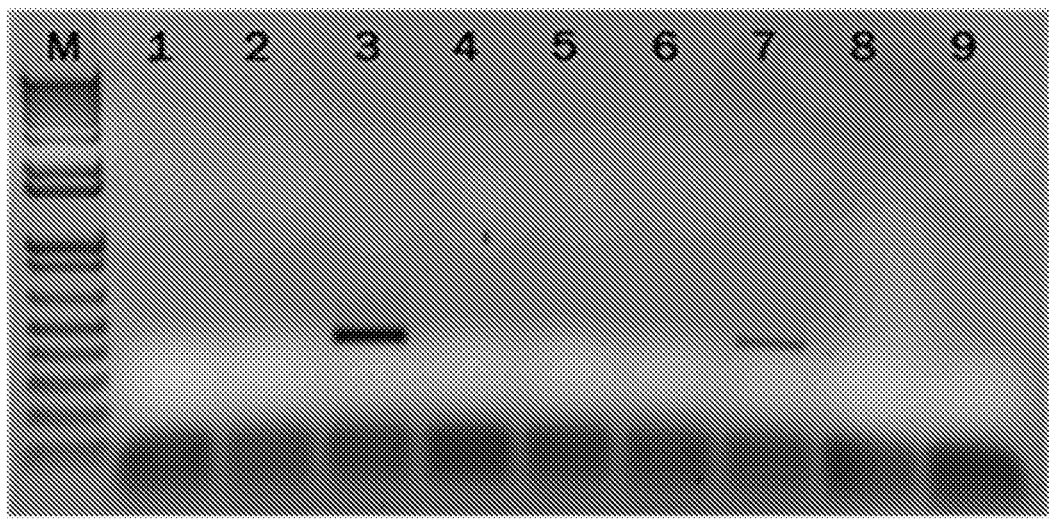

Clones of Rep78/52 or VP1/2/3 expressing *C. reinhardtii* cells were checked for the genomic integration of the plasmid DNA with the help of colony PCR as shown in FIG. 7. Here, individual clones were resuspended in distilled water and incubated at 95° C. for 10 min. This step ruptured the cell as well as the nuclear membrane, releasing the genomic material in the suspension. This is further utilized as the DNA template for the PCR amplification using primers specific to individual transgene sequences. Colony PCR conditions used in this step are as follows:

As colony PCR only confirms the integration of the plasmid DNA, it does not provide information regarding the functionality of the integrated expression cassette. In order to confirm functionality, the positive clones of Rep78/52 and VP1/2/3 lines were further screened for their ability to grow in the Zeocin containing liquid medium. As the transgene and the zeocin resistance gene reporter utilize the same promoter, zeocin resistance of *C. reinhardtii* clones suggests the proper expression and functioning of the reporter and henceforth the expression of the downstream transgene.

Figure 8:
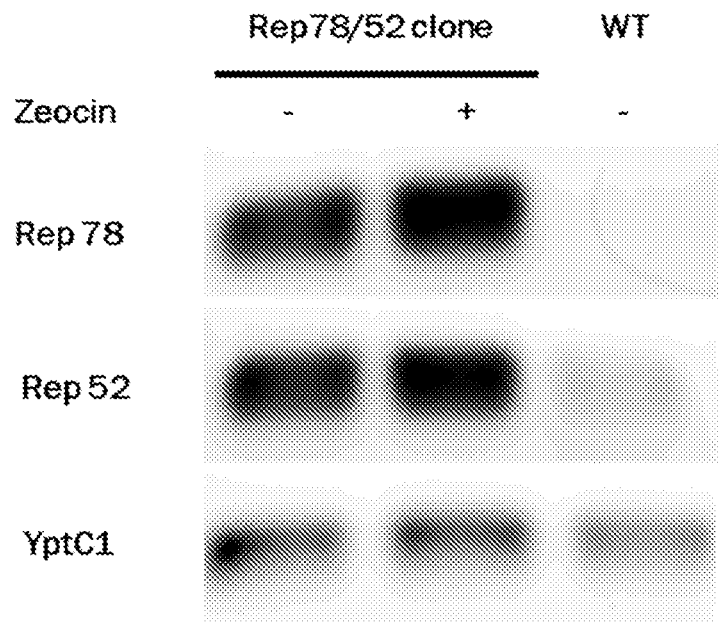
FIG. 8 demonstrates confirmation of expression of Rep78/52 and VP1/2/3 in *C. reinhardtii* cells.
Figure 8:
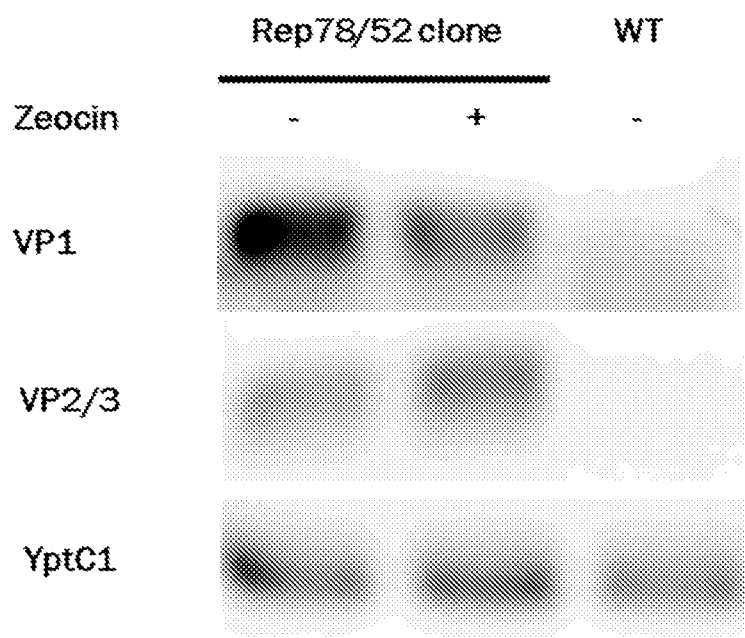

Expression of the transgenes from the Zeocine resistant clones was further analyzed by the confirming the presence of mRNA transcripts for the respective genes. Total RNA was extracted from the Zeocin resistant Rep78/52 positive and VP1/2/3 positive *C. reinhardtii* clones using Trizol. It was further converted to cDNA with the help of RT2 First strand synthesis kit from Qiagen. cDNA from these clones was further amplified in a standard PCR reaction with the help of primers specific to Rep78, Rep52, VP1 and VP2/3. Non-transformed *C. reinhardtii* cell RNA was utilized as a negative control. Presence of specific, amplified DNA fragments, corresponding to the viral transgenes, only in the positive clones confirmed that the viral transgenes were stably expressed in the Zeocin resistant *C. reinhardtii* transformants as shown in FIG. 8. RNA from the same clones was also isolated and grown in the medium with no antibiotic selection. Presence of the same amplified DNA fragments corresponding to the viral transgenes from these cells indicates that once integrated, the transgenes are stably expressed even without the need of selectable marker Positive transformants containing all the components for the rAAV production are further amplified in TAP medium in shake flasks at the ambient temperature of 26° C. under constant illumination using moderate light intensities of cool fluorescent while light (50±10 µE m-2 s-1). Algal mass is finally harvested and lysed and fractionated by CsCl gradient centrifugation to purify rAAV viral particles.

After establishment of *C. reinhardtii* lines stably expressing either Rep or Cap genes, these cells are further transformed with the complementary plasmids by sequential transformation to obtain the *C. reinhardtii* cells expressing both Rep and Cap genes. Transformants are obtained on selective media plates and analyzed for the presence of all the plasmids by PCR.

To reduce the number of steps required to obtain the final desired microalgal transformant stably expressing all the Rep and Cap genes in optimal stoichiometric amounts, different combinations of the plasmids containing different promoters, resistance markers as well as mono or polycistronic mRNAs are utilized.

These experiments demonstrate successful construction of single as well as dual microalgal expression cassettes for the expression of codon optimized viral Rep genes and Cap genes. *C. reinhardtii* cultures were also optimized and established and these cells were successfully transformed and lines that stably express viral Rep genes and Cap genes were established.

In order to reduce the number of algal transformants to screen when generating *C. reinhardtii* cell lines expressing rep and cap, microalgal plasmids harboring different resistance markers are used. Individual AAV transgenes are cloned plasmids containing different antibiotic resistance genes. Thus, utilizing multi-antibiotic resistance as a parameter, the number of algal transformants required to be screened is reduced drastically.

Example 3

Plasmid Generation for Microalgal AAV Production

The multiple gene products for AAV production, Rep78, Rep52, VP1 and VP2/3 are individually expressed and are codon optimized and cloned into algal expression plasmids as described above in Example 1. These plasmids can be obtained commercially from Invitrogen as well as *Chlamydomonas* resource center as well as other sources.

Example 4

Gene Stacking by Gametogenesis

Figure 9:
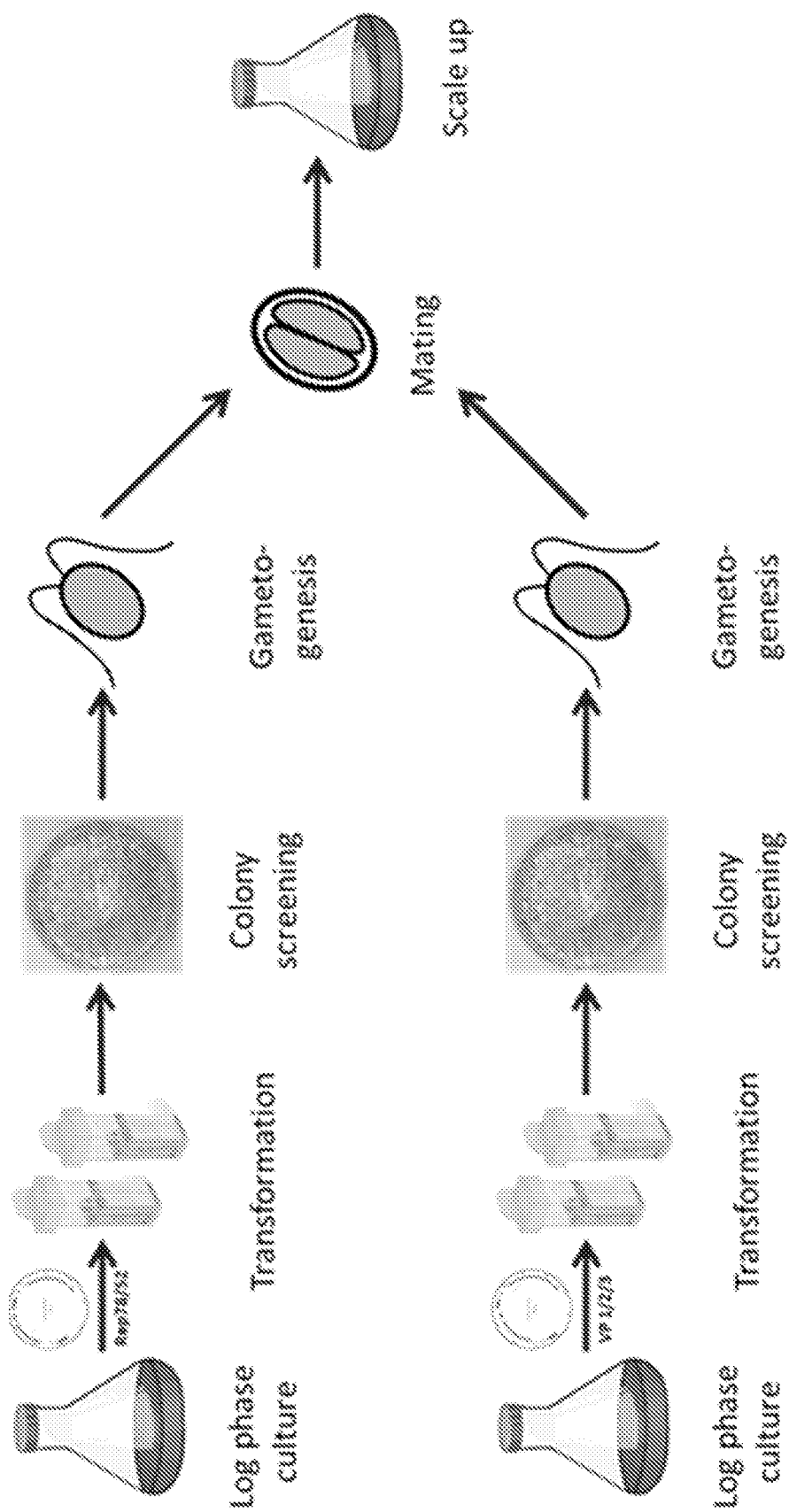
FIG. 9 provides work flow for gene stacking approach by gametogenesis to generate *C. reinhardtii* cells stable expressing REP 78/52 and VP1/2/3.

Sequential gene stacking approach will be utilized to generate the stable lines of *C. reinhardtii* cells expressing AAV Rep/Cap proteins (FIG. 9). In this case, *C. reinhardtii* cells stably expressing Rep78/52 or VP1/2/3 are generated and then the same line would be further transformed with the other Cap or Rep constructs.

An alternate strategy to generate the *C. reinhardtii* cells expressing both Rep and Cap genes simultaneously using gametogenesis for the gene stacking was carried out. *C. reinhardtii* is a haploid organism that reproduces vegetatively in normal growth conditions. Under certain conditions, vegetative cells differentiate into haploid gametes of two forms, mating type plus (mt+) or mating type minus (mt−). Two gametes then fuse to form a diploid zygospore which can then reproduce vegetatively in normal conditions again. It is successfully shown that genes integrated into separate chromosomes of separate mating types are assorted resulting in progeny with either parents. This strategy results in generation of transgenic lines of microalgal strain of either mating types expressing different viral transgenes. These lines are further crossed together to a single progeny expressing all the required viral transgenes (FIG. 9).

*C. reinhardtii* cells corresponding to mating type mt+ and mt− are obtained from *Chlamydomonas* resource center and transformed with the AAV transgene plasmids to generate the haploid transgenic lines that are subjected to gametogenesis to obtain the final microalgal transgenic line expressing all Rep and Cap proteins. To obtain the most efficient microalgal strain producing the optimal levels of individual AAV transgenes, uni-cistronic as well as polycistronic plasmids with different algal promoters and antibiotic resistances will also be utilized for the gene stacking by gametogenesis.

Example 4

Functional Analysis of Microalgal rAAV Vector In Vivo

To determine the efficacy of the rAAV vector produced in the microalgal system, cohorts of wild-type mice are intravenously injected with various titers of microalgal rAAV at neonatal or adult stages. Transduction efficiency of microalgal rAAV is analyzed by immunohistochemistry, Western blot analysis and in situ hybridization.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

We claim:

1. A eukaryotic microalgae that produces a recombinant adeno-associated virus (rAAV).

2. The eukaryotic microalgae of claim 1 wherein the eukaryotic microalgae is *Chlamydomonas reinhardtii, Chlorella vulgaris, Chlorella ellipsoidea, Chlorella sorokiniana, Chlorella kessleri, Volvox carteri, Dunaliella salina, Ostreococcus tauri, Phaeodactylum tico, Gonium pectoral*, and *Cyanidiosschyzon merolae*.

3. The eukaryotic microalgae of claim 1 or 2 wherein the eukaryotic microalgae is *Chlamydomonas reinhardtii*.

4. The eukaryotic microalgae of claim 1, wherein the microalgae is transformed with a polynucleotide construct comprising (i) a polynucleotide sequence encoding Rep 78 protein, Rep 52 protein, VP1 protein or VP2/3 protein or (ii) one or more polynucleotide sequences encoding Rep78 protein, Rep52 protein, VP1 protein and VP2/VP3 protein or (iii) one or more polynucleotide sequences encoding Rep78 protein, Rep52 protein, VP1 protein, VP2 protein and VP3 protein.

5. The eukaryotic microalgae of claim 4 wherein the construct further comprises an AAV inverted terminal repeat (ITR) and 3' AAV ITR, and helper functions for generating a productive AAV infection.

6. The eukaryotic microalgae of claim 1, wherein the microalgae is transformed with one or more polynucleotide constructs wherein each polynucleotide construct comprises at least one polynucleotide sequence encoding Rep 78 protein, Rep 52 protein, VP1 protein, VP2/3 protein, VP2 protein or VP3 protein.

7. The eukaryotic microalgae of claim 6 wherein the construct further comprises an AAV inverted terminal repeat (ITR) and 3' AAV ITR, and helper functions for generating a productive AAV infection.

8. The eukaryotic microalgae of claim 6, wherein the recombinant AAV is AAV1, AAV2, AAV3, AAV4, AAV5, AAV6, AAV7, AAV8, AAV9, AAV10, AAV11, AAV12 or AAV13.

9. The eukaryotic microalgae of claim 6, wherein the recombinant AAV is AAV9.

10. The eukaryotic microalgae of claim 1, wherein the recombinant AAV is AAV1, AAV2, AAV3, AAV4, AAV5, AAV6, AAV7, AAV8, AAV9, AAV10, AAV11, AAV12 or AAV13.

11. The eukaryotic microalgae of claim 1, wherein the recombinant AAV is AAV9.

12. A method of producing a recombinant virus, wherein the recombinant virus is a recombinant adeno-associated virus (rAAV), comprising the steps of growing an eukaryotic microalgae producing the recombinant virus.

13. The method of claim 12 wherein the eukaryotic microalgae is transformed with a polynucleotide sequence expressing the recombinant virus.

14. The method of claim 12 further comprising the step of purifying the recombinant virus.

15. The method of claim 12, wherein the eukaryotic microalgae is *Chlamydomonas reinhardtii, Chlorella vulgaris, Chlorella ellipsoidea, Chlorella sorokiniana, Chlorella kessleri, Volvox carteri, Dunaliella saline, Ostreococcus tauri, Phaeodactylum tico, Gonium pectoral*, and *Cyanidiosschyzon merolae*.

16. The method of claim 12, wherein the eukaryotic microalgae is *Chlamydomonas reinhardtii*.

17. The method of claim 12, wherein the recombinant AAV is AAV1, AAV2, AAV3, AAV4, AAV5, AAV6, AAV7, AAV8, AAV9, AAV10, AAV11, AAV12 or AAV13.

18. The method of claim 12, wherein the recombinant AAV is AAV9.

19. The method of claim 12, wherein the eukaryotic microalgae is transformed with a polynucleotide construct comprising (i) a polynucleotide nucleotide sequence encoding Rep 78 protein, Rep 52 protein, VP1 protein or VP2/3 protein or (ii) one or more polynucleotide sequences encoding Rep78 protein, Rep52 protein, VP1 protein and VP2/VP3 protein or (iii) one or more polynucleotide sequences encoding Rep78 protein, Rep52 protein, VP1 protein, VP2 protein and VP3 protein.

20. The method of claim 19 wherein the construct further comprises an AAV inverted terminal repeat (ITR) and 3' AAV ITR, and helper functions for generating a productive AAV infection.

21. The method of claim 12, wherein the eukaryotic microalgae is transformed with one or more polynucleotide constructs wherein each construct comprises at least one polynucleotide sequence encoding Rep 78 protein, Rep 52 protein, VP1 protein, VP2/3 protein, VP2 protein or VP3 protein.

22. The method of claim 21 wherein the construct further comprises an AAV inverted terminal repeat (ITR) and 3' AAV ITR, and helper functions for generating a productive AAV infection.

23. The method of claim 21, wherein the recombinant AAV is AAV1, AAV2, AAV3, AAV4, AAV5, AAV6, AAV7, AAV8, AAV9, AAV10, AAV11, AAV12 or AAV13.

24. The method of claim 21, wherein the recombinant AAV is AAV9.

* * * * *